US010202618B2

(12) United States Patent
Hammond et al.

(10) Patent No.: US 10,202,618 B2
(45) Date of Patent: Feb. 12, 2019

(54) METHOD OF TREATING TYPE I DIABETES USING AN AAV VECTOR ENCODING URACORTIN 2

(71) Applicant: The Regents of the University of California, Oakland, CA (US)

(72) Inventors: H. Kirk Hammond, La Jolla, CA (US); Mei Hua Gao, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/625,719

(22) Filed: Jun. 16, 2017

(65) Prior Publication Data

US 2018/0010148 A1 Jan. 11, 2018

Related U.S. Application Data

(63) Continuation-in-part of application No. 14/378,645, filed as application No. PCT/US2013/025997 on Feb. 13, 2013.

(60) Provisional application No. 61/598,772, filed on Feb. 14, 2012.

(51) Int. Cl.

| | |
|---|---|
| *A01N 63/00* | (2006.01) |
| *C12N 15/861* | (2006.01) |
| *A61K 38/22* | (2006.01) |
| *C07K 14/575* | (2006.01) |
| *C07K 14/65* | (2006.01) |
| *C12N 15/86* | (2006.01) |
| *A61K 31/436* | (2006.01) |
| *A61K 31/65* | (2006.01) |
| *A61K 47/69* | (2017.01) |
| *C07K 14/075* | (2006.01) |
| *A61K 38/25* | (2006.01) |
| *A61K 38/30* | (2006.01) |
| *A61K 38/52* | (2006.01) |
| *A61K 48/00* | (2006.01) |

(52) U.S. Cl.
CPC .......... *C12N 15/861* (2013.01); *A61K 31/436* (2013.01); *A61K 31/65* (2013.01); *A61K 38/2228* (2013.01); *A61K 47/6901* (2017.08); *C07K 14/075* (2013.01); *C07K 14/57509* (2013.01); *C07K 14/65* (2013.01); *C12N 15/86* (2013.01); *A61K 38/2221* (2013.01); *A61K 38/2242* (2013.01); *A61K 38/25* (2013.01); *A61K 38/30* (2013.01); *A61K 38/52* (2013.01); *A61K 48/00* (2013.01); *A61K 48/005* (2013.01); *C12N 2710/10343* (2013.01); *C12N 2750/14143* (2013.01); *C12N 2830/003* (2013.01)

(58) Field of Classification Search
USPC ....................................................... 424/93.2
See application file for complete search history.

(56) References Cited

U.S. PATENT DOCUMENTS 6,214,797 B1 4/2001 Vale, Jr. et al.

FOREIGN PATENT DOCUMENTS

| NZ | 523803 A | 8/2004 |
|---|---|---|
| WO | 0134208 A1 | 5/2001 |
| WO | 0212307 A1 | 2/2002 |
| WO | 03062277 A1 | 1/2003 |
| WO | 2006086402 A2 | 8/2006 |
| WO | 2006121532 A2 | 11/2006 |
| WO | 2007133572 A2 | 11/2007 |
| WO | 2008047241 A2 | 4/2008 |
| WO | 2009065080 A1 | 5/2009 |
| WO | 2009088786 A1 | 7/2009 |
| WO | 2009140657 A2 | 11/2009 |
| WO | 2010053990 A2 | 5/2010 |
| WO | 2011057027 A2 | 5/2011 |

OTHER PUBLICATIONS

Edelstein (Journal Gene Med., 2004, vol. 6, p. 597-602).*
Camilleri, Extended European Search Report for EP 13749674.1 dated Dec. 16, 2015.
Dschietzig et al, "A pilot safety and dose-finding trial of intravenous recombinant human relaxin (rhRlx) in compensated congestive heart failure" European Journal of Heart Failure, Jun. 1, 2007 v 6, n 1, p. 90.
Ponikowski et al, "Design of the RELAXin in acute heart failure study" American Heart Journal, Feb. 1, 2012, v 163, n 2, p. 149.
Teerlink et al, "Seralaxin, recombinant human relaxin-2, for treatment of acute heart failure (RELAX-AHF): a randomised, placebo-controlled trial for the RELAXin in Acute Heart Failure (RELAX-AHF) Investigators" The Lancet, Nov. 7, 2012 v 381, n 9860, p. 29-39.
Meili-Butz et al, "Chronic Administration of Urocortin 2 in Hypertension-Induce Hypertrophy: Effects on Intracellular Calcium Handling and Hemodynamics" Database BioSis, Nov. 2009, v 120, n 18, suppl. 2, p. S868.

(Continued)

*Primary Examiner* — Michael C Wilson
(74) *Attorney, Agent, or Firm* — Greer, Burns & Crain, LTD.; Gregory P. Einhorn

(57) ABSTRACT

In alternative embodiments, the invention provides methods for treating, ameliorating or protecting (preventing) an individual or a patient against a disease, an infection or a condition responsive to an increased paracrine polypeptide level in vivo comprising: providing a paracrine polypeptide-encoding nucleic acid or gene operatively linked to a transcriptional regulatory sequence; or an expression vehicle, a vector, a recombinant virus, or equivalent, having contained therein a paracrine-encoding nucleic acid or gene, and the expression vehicle, vector, recombinant virus, or equivalent can express the paracrine-encoding nucleic acid or gene in a cell or in vivo; and administering or delivering the paracrine polypeptide -encoding nucleic acid or gene operatively linked to a transcriptional regulatory sequence, or the expression vehicle, vector, recombinant virus, or equivalent, to an individual or a patient in need thereof, thereby treating, ameliorating or protecting (preventing) the individual or patient against the disease, infection or condition responsive to an increased paracrine polypeptide level.

8 Claims, 28 Drawing Sheets

(56) References Cited

OTHER PUBLICATIONS

Pepe et al, "Intramyocardial VEGF-B167 Gene Delivery Delays the Progression Towards Congestive Failure in Dogs with Pacing-Induced Dilated Cardiomyopathy" Circulation Research, Jun. 25, 2010, v 106, n 12, p. 1893-1903.
Choi, Written Opinion for PCT/US2013/025997, dated May 31, 2013.
Moon, International Preliminary Report on Patentability for PCT/US2013/025997, dated Aug. 28, 2014.
Meili-Butz et al, "Acute effects of urocortin 2 on cardiac function and propensity for arrhythmias in an animal model of hypertension-induced left ventricular hypertrophy and heart failure", European Journal of Heart Failure, Aug. 2010, v 12, n 8, p. 797-807.
Rademaker et all, "Urocortin 2 sustains haemodynamic and renal function during introduction of beta-blockade in experimental heart failure", Journal of Hypertension, Sep. 2011, v 29, n 9, p. 1787-1795.
Lai et al, "Intravenous delivery of AAV9 encoding urocortin 2 increases cardiac function in normal mice", The FASEB Journal, Apr. 2012, v 26 n 1, suppl. 1134.1.
Dieterle et al, "Immediate and sustained blood pressure lowering by urocortin 2: a novel approach to antihypertensive therapy?", Hypertension AHA, Mar. 2009, v 53, p. 739-744.
Rademaker et al, "Prolonged Urocortin 2 Administration in Experimental Heart Failure: Sustained Hemodynamic, Endocrine, and Renal Effects", Hypertension AHA, Jun. 2011, v 57, n 6, p. 1136-1144.
Johnson-Saliba et al, "Gene Therapy: Optimising DNA Delivery to the Nucleus", Current Drug Targets, Dec. 2001, v 2, n 4, p. 371-399.
Luo et al, "Synthetic DNA delivery systems", Nature Biotechnology, Jan. 2000, v 18, p. 33-37.
Deonarian, "Ligand-targeted receptor-mediated vectors for gene delivery", Expert Opinion on Therapeutic Patents, 1998, v 8, n 1, 53-69.
Palu et al, "In pursuit of new developments for gene therapy of human diseases.", Journal of Biotechnology, Feb. 1999, v 68, p. 1-13.
Pfeifer et al, "Gene Therapy: Promises and Problems", Annual Review of Genomics and Human Genetics, Sep. 2001, v 2, p. 177-211.
Sholi et al, "Current Status of Delivery Systems to Improve Target Efficacy of Oligonu-cleotides", Current Pharmaceutical Design, Mar. 2004, v 10, n 7, p. 785-796.
Verma et al, "Gene therapy—promises, problems and prospects", Nature International Journal of Science, Sep. 1997, v 389, p. 239-242.
Edelstein et al, "Gene therapy clinical trials worldwide 1989-2004—an overview", The Journal of Gene Medicine, Jun. 2004, v 6, n 6, p. 597-602.
Gaffney et al., "Cardiovascular gene therapy: current status and therapeutic potential" British Journal of Pharmacology, 2007, v. 152, pp. 175-188.
Wang et al. "Adeno-associated virus serotype 8 efficiently delivers genes to muscle and heart" Nature Biotechnology, Mar. 2005, v 23, n 3, p. 321-328.
Davis et al., "Urocortin 2 infusion in human heart failure" European Heart Journal, 2007, v 28, n 21, p. 2589-2597.
Mizukami, Journal of Clinical and Experimental Medicine Hematopathology State of Arts ver 3 2005 p. 541-544.
Torii, Notice of Reasons for Rejection for JP Patent Application 2014-556826, dated Jul. 13, 2018.
Rademaker et al. "Urocortin 3: haemodynamic, hormonal, and renal effects in experimental heart failure" European Heart Journal, 2006, v 27, p. 2088-2098.
Camilleri, European Search Report for EP 17208610 dated Mar. 26, 2018.
NCT01120210, "A study to investigate the safety, tolerability, pharmacodynamics and pharmacokinetics of an intravenous solution of JNJ-39588146 or placebo in patients with heart failure".
Gaffney et al., "Cardiovascular gene therapy: current status and therapeutic potential" Br J. Pharmacol, Sep. 2007, v 152, n 2, p. 175-188.
Lyon et al., "Gene therapy: targeting the myocardium" Heart, 2008, v 94, n 1, p. 89-99.
Ray, Examination report No. 1 for Australian Patent Application 2018200719, dated Oct. 29, 2018.

\* cited by examiner

FIG. 4D

| Table 4. Echocardiography: Effects of Skeletal Muscle IGFI Expression in CHF | | | | | | | |
|---|---|---|---|---|---|---|---|
| | IGF-Off (9) | | | IGF-On (10) | | | |
| | 5w after MI | 10w after MI | Change (%) | 5w after MI | 10w after MI | Change (%) | p |
| HR -bpm- | 341±16 | 340±9 | -0.7±14.1 | 355±10 | 351±10 | -3.9±10.2 | 0.85 |
| EDD -mm- | 10.0±0.2 | 9.9±0.4 | -0.1±0.3 | 9.8±0.3 | 9.2±0.3 | -0.1±0.4 | 0.56 |
| ESD -mm- | 7.9±0.4 | 8.2±0.5 | 0.3±0.3 | 7.9±0.5 | 7.1±0.4 | -0.9±0.4 | 0.03 |
| EF (%) | 41±3 | 39±3 | -1.4±2.4 | 37±4 | 45±2 | +8.6±3.1 | 0.02 |

AAV5 vs AAV9 ($5 \times 10^{11}$ gc, IV)

Liver

Heart

FIG. 26

| Table 5. Effects of Activation of Skeletal Muscle IGFI Expression in CHF | | | | |
|---|---|---|---|---|
| | | IGF-Off (n=10) | IGF-On (n=10) | p |
| HR (beats/min) | Basal<br>Dobutamine | 377±42<br>373±29 | 364±83<br>395±10 | 0.79 |
| CO<br>(ml/min) | Basal<br>Dobutamine | 10.3±2.2<br>15.8±2.4 | 16.3±1.8<br>23.2±2.8 | 0.007 |
| SW (ml·mmHg) | Basal<br>Dobutamine | 1.6±0.4<br>3.8±0.8 | 4.1±0.6<br>6.4±1.2 | 0.003 |
| LV +dP/dt<br>(mmHg/s) | Basal<br>Dobutamine | 4,237±630<br>6,842±913 | 6,337±687<br>12,974±1,061 | <0.0001 |
| LV -dP/dt<br>(mmHg/s) | Basal<br>Dobutamine | -3,453±494<br>-6,036±1,197 | -4,564±409<br>-8,518±1,056 | 0.030 |
| Systolic Pressure<br>(mmHg) | Basal<br>Dobutamine | 104±12<br>113±9 | 143±11<br>163±8 | 0.011 |
| Mean Pressure<br>(mmHg) | Basal | 82±13 | 110±8 | 0.07 |
| SVR (Wood Units) | Basal | 7.5±1.3 | 6.8±0.5 | 0.23 |
| HR, heart rate; CO, cardiac output; SW, stroke work.<br>Data denote mean ±SE.<br>Probability values from 2-way ANOVA, showing IGFI effect. Reference 5 | | | | | ns
METHOD OF TREATING TYPE I DIABETES USING AN AAV VECTOR ENCODING URACORTIN 2

CROSS-REFERENCE TO RELATED APPLICATIONS

This United States utility patent application is a continuation-in-part (CIP) of U.S. Ser. No. 14/378,645, filed Aug. 13, 2014 (now pending), which is a § 371 national phase of PCT international patent application no. PCT/US2013/025997, having an international filing date of Feb. 13, 2013, which claims benefit of priority to U.S. Provisional Patent Application Ser. No. 61/598,772, filed Feb. 14, 2012. The aforementioned applications are expressly incorporated herein by reference in their entirety and for all purposes.

STATEMENT AS TO RIGHTS TO INVENTIONS MADE UNDER FEDERALLY SPONSORED RESEARCH

This invention was made with government support under grant no. HL088426 awarded by the National Institutes of Health (NIH), DHHS. The government has certain rights in the invention.

TECHNICAL FIELD

This invention relates to cellular and molecular biology and medicine. The invention provides compositions and in vitro and ex vivo methods. In alternative embodiments, the invention provides methods for treating, ameliorating or protecting (preventing) an individual or a patient against a disease, an infection or a condition responsive to an increased or a sustained paracrine polypeptide level in vivo comprising: providing a paracrine polypeptide-encoding nucleic acid or gene operatively linked to a transcriptional regulatory sequence; or an expression vehicle, a vector, a recombinant virus, or equivalent, having contained therein a paracrine-encoding nucleic acid, gene, transcript or message, and the expression vehicle, vector, recombinant virus, or equivalent can express the paracrine-encoding nucleic acid, gene, transcript or message in a cell or in vivo; and administering or delivering the paracrine polypeptide-encoding nucleic acid, gene, transcript or message operatively linked to a transcriptional regulatory sequence, or the expression vehicle, vector, recombinant virus, or equivalent, to an individual or a patient in need thereof, thereby treating, ameliorating or protecting (preventing) the individual or patient against the disease, infection or condition responsive to an increased paracrine polypeptide level.

BACKGROUND

Recently an intravenous injection of a virus vector encoding human Factor IX, which is deficient in Hemophilia B was shown to increase Factor IX concentration in the serum of subjects with Hemophilia B to a degree that lowered their requirements for exogenous Factor IX infusion. However: 1) this protein was not under regulated expression, and therefore, did not enable optimal tailoring of levels of the transgene in the serum, 2) this system did not provide for a means to turn off transgene expression in case of undesired or unexpected effects, and 3) the gene, Factor IX, was not a paracrine gene, and had no beneficial cardiovascular effects, and therefore, could not be used to treat heart disease.

SUMMARY

The invention provides methods for treating, ameliorating or protecting (preventing) an individual or a patient against any disease, infection or condition responsive to an increased paracrine polypeptide level in vivo. In alternative embodiments, the invention provides methods for treating, ameliorating or protecting (preventing) against a disease, an infection or a condition responsive to an increased or sustained peptide or paracrine polypeptide level in vivo comprising:

(a) (i) providing a paracrine polypeptide-encoding nucleic acid or gene operatively linked to a transcriptional regulatory sequence; or an expression vehicle, a vector, a recombinant virus, or equivalent, having contained therein a paracrine-encoding nucleic acid or gene, or a paracrine polypeptide-expressing nucleic acid, transcript or message, and the expression vehicle, vector, recombinant virus, or equivalent can express the paracrine-encoding nucleic acid, gene, transcript or message in a cell or in vivo; and (ii) administering or delivering the paracrine polypeptide-encoding nucleic acid, gene, transcript or message operatively linked to a transcriptional regulatory sequence, or the expression vehicle, vector, recombinant virus, or equivalent, to the cell, or an individual or a patient in need thereof, thereby treating, ameliorating or protecting (preventing) the individual or patient against the disease, infection or condition responsive to an increased or a sustained paracrine polypeptide level;

(b) the method of (a), wherein the expression vehicle, vector, recombinant virus, or equivalent is or comprises:

an adeno-associated virus (AAV), a lentiviral vector or an adenovirus vector, an AAV serotype AAV5, AAV6, AAV8 or AAV9, a rhesus-derived AAV, or the rhesus-derived AAV AAVrh.10hCLN2, an AAV capsid mutant or AAV hybrid serotype, an organ-tropic AAV, or a cardiotropic AAV, or a cardiotropic AAVM41 mutant, wherein optionally the AAV is engineered to increase efficiency in targeting a specific cell type that is non-permissive to a wild type (wt) AAV and/or to improve efficacy in infecting only a cell type of interest, and optionally the hybrid AAV is retargeted or engineered as a hybrid serotype by one or more modifications comprising: 1) a transcapsidation, 2) adsorption of a bi-specific antibody to a capsid surface, 3) engineering a mosaic capsid, and/or 4) engineering a chimeric capsid;

(c) the method of (a), wherein the paracrine-encoding nucleic acid, gene, transcript or message is operatively linked to a regulated or inducible transcriptional regulatory sequence;

(d) the method of (c), wherein the regulated or inducible transcriptional regulatory sequence is a regulated or inducible promoter, wherein optionally a positive (an activator) and/or a negative (a repressor) modulator of transcription and/or translation is operably linked to the paracrine polypeptide-encoding nucleic acid, gene, transcript or message;

(e) the method of any of (a) to (d), wherein administering the paracrine polypeptide-encoding nucleic acid, gene, transcript or message operatively linked to a transcriptional regulatory sequence, or the expression vehicle, vector, recombinant virus, or equivalent, to an individual or a patient in need thereof results in a paracrine protein being released into the bloodstream or general circulation, or an increased or sustained expression of the paracrine protein in the cell, wherein optionally the release or increased or sustained expression of the paracrine protein is dependent on activation of an inducible promoter, or de-repression of a repressor, operably linked to the paracrine polypeptide-encoding nucleic acid, gene, transcript or message; or (f) the method of any of (a) to (e), wherein the disease, infection or condition responsive to an increased paracrine polypeptide level in vivo is a cardiac contractile dysfunction; a congestive heart failure (CHF); a cardiac fibrosis; a cardiac myocyte disease, dysfunction or apoptosis; a pulmonary hypertension; a heart, skin, liver, lung, muscle, nerve, brain or kidney disease, cancer or dysfunction; a cancer or a neoplasia; or, a hemophilia or a Hemophilia B.

In alternative embodiments of methods of the invention:

(a) the paracrine-encoding nucleic acid or gene operatively linked to the transcriptional regulatory sequence; or the expression vehicle, vector, recombinant virus, or equivalent, is administered or delivered to the individual or a patient in need thereof, by oral, intramuscular (IM) injection, by intravenous (IV) injection, by subcutaneous (SC) or intradermal injection, by intrathecal injection, by intra-arterial (IA) injection, by intracoronary injection, by inhalation, or by a biolistic particle delivery system, or by using a "gene gun", air pistol or a HELIOS™ gene gun (Bio-Rad Laboratories, Hercules, Calif.); or (b) the paracrine-encoding nucleic acid or gene operatively linked to the transcriptional regulatory sequence; or the expression vehicle, vector, recombinant virus, or equivalent, is administered or delivered to the individual or a patient in need thereof, by introduction into any tissue or fluid space within the body that is adjacent to or is drained by the bloodstream, such that the encoded protein may be secreted from cells in the tissue and released into the bloodstream.

In alternative embodiments of methods of the invention: the paracrine polypeptide or peptide is or comprises: a mammalian cardiotonic peptide, a growth factor, a Serelaxin, a Relaxin-2, a Urocortin-2 (UCn-2), a Urocortin-1 (UCn-1), a Urocortin-3 (UCn-3), a Brain Natriuretic Peptide, a Prostacyclin Synthase, a Growth Hormone, an Insulin-like Growth Factor-1, or any combination thereof; or, a human cardiotonic peptide, a human growth factor, a Serelaxin, a Relaxin-2, a Urocortin-2, a Urocortin-1, a Urocortin-3, a Brain Natriuretic Peptide, a Prostacyclin Synthase, a Growth Hormone, an Insulin-like Growth Factor-11, or any combination thereof.

In alternative embodiments of methods of the invention: the paracrine polypeptide is a Urocortin, a Urocortin-2, Urocortin-1, a Urocortin-3, a Relaxin-2 or a Brain Natriuretic Peptide and the disease or condition is a congestive heart failure (CHF); or the paracrine polypeptide is Prostacyclin Synthase and the disease or condition a pulmonary hypertension and the disease or condition is a congestive heart failure (CHF); or the paracrine polypeptide is Prostacyclin Synthase and the disease or condition a pulmonary hypertension.

In alternative embodiments of methods of the invention:

(a) the individual, patient or subject is administered a stimulus or signal that induces expression of the paracrine-expressing nucleic acid or gene, or induces or activates a promoter (e.g., operably linked to the paracrine-expressing nucleic acid or gene) that induces expression of the paracrine-expressing nucleic acid or gene;

(b) the individual, patient or subject is administered a stimulus or signal that induces synthesis of an activator of a promoter, optionally a paracrine-expressing nucleic acid or gene-specific promoter (e.g., operably linked to the paracrine-expressing nucleic acid or gene);

(c) the individual, patient or subject is administered a stimulus or signal that induces synthesis of a natural or a synthetic activator of the paracrine-expressing nucleic acid or gene or the paracrine-expressing nucleic acid or gene-specific promoter, wherein optionally the natural activator is an endogenous transcription factor;

(d) the method of (c), wherein the synthetic activator is a zinc-finger DNA binding protein designed to specifically and selectively turn on an endogenous or exogenous target gene, wherein optionally the endogenous target is a gene paracrine-expressing nucleic acid or gene or an activator of a paracrine-expressing nucleic acid or gene, or an activator of a promoter operatively linked to a paracrine-expressing nucleic acid or gene;

(e) the method of any of (a) to (c), wherein the stimulus or signal comprises a biologic, a light, a chemical or a pharmaceutical stimulus or signal;

(f) the individual, patient or subject is administered a stimulus or signal that stimulates or induces expression of a post-transcriptional activator of a paracrine-expressing nucleic acid or gene, or an activator of a promoter operatively linked to a paracrine-expressing nucleic acid or gene, or (g) the individual, patient or subject is administered a stimulus or signal that inhibits or induces inhibition of a transcriptional repressor or a post-transcriptional repressor of a paracrine-expressing nucleic acid or gene.

In alternative embodiments of methods of the invention: the chemical or pharmaceutical that induces expression of the paracrine-expressing nucleic acid or gene, or induces expression of the regulated or inducible promoter operatively linked to the paracrine-expressing nucleic acid or gene, is an oral antibiotic, a doxycycline or a rapamycin; or a tet-regulation system using doxycycline is used to induce expression of the paracrine-expressing nucleic acid or gene, or an equivalent thereof.

In alternative embodiments of methods of the invention: the paracrine-expressing nucleic acid or gene or the expression vehicle, vector, recombinant virus, or equivalent, is formulated in a liquid, a gel, a hydrogel, a powder or an aqueous formulation.

In alternative embodiments of methods of the invention: the paracrine-expressing nucleic acid or gene or the expression vehicle, vector, recombinant virus, or equivalent, or the urocortin-2 (UCn-2) peptide or polypeptide, is formulated in a vesicle, liposome, nanoparticle or nanolipid particle (NLP) or equivalents, or formulated for delivery using a vesicle, liposome, nanoparticle or nanolipid particle (NLP) or equivalents.

In alternative embodiments of methods of the invention: the paracrine-expressing nucleic acid or gene or the expression vehicle, vector, recombinant virus, or equivalent, is formulated in, or inserted or transfected into, an isolated or cultured cell, and optionally the cell is a mammalian cell, a cardiac cell, or a human cell, a non-human primate cell, a monkey cell, a mouse cell, a rat cell, a guinea pig cell, a rabbit cell, a hamster cell, a goat cell, a bovine cell, an equine cell, an ovine cell, a canine cell or a feline cell.

In alternative embodiments of methods of the invention: the paracrine-expressing nucleic acid or gene or the expression vehicle, vector, recombinant virus, or equivalent, or the urocortin-2 (UCn-2) peptide or polypeptide, is formulated as a pharmaceutical or a sterile formulation.

In alternative embodiments of methods of the invention: the paracrine-expressing nucleic acid or gene or the expression vehicle, vector, recombinant virus, or equivalent, or the urocortin-2 (UCn-2) peptide or polypeptide, is formulated or delivered with, on, or in conjunction with a product of manufacture, an artificial organ or an implant.

In alternative embodiments of methods of the invention: the paracrine-expressing nucleic acid or gene or the expression vehicle, vector, recombinant virus, or equivalent expresses a paracrine polypeptide in vitro or ex vivo.

In alternative embodiments the invention provides methods for treating, ameliorating or protecting (preventing) an individual or a patient against a paracrine-responsive pathology, infection, disease, illness, or condition, comprising practicing a method of the invention.

In alternative embodiments the invention provides methods for treating, ameliorating or protecting (preventing) a cardiac contractile dysfunction; a congestive heart failure (CHF); a cardiac fibrosis; a cardiac myocyte disease, dysfunction or apoptosis; a pulmonary hypertension; a heart, skin, liver, lung, muscle, nerve, brain or kidney disease, cancer or dysfunction; a cancer or a neoplasia; or, a hemophilia or a Hemophilia B, comprising practicing a method of the invention.

In alternative embodiments, the invention provides methods of treating, ameliorating or protecting (preventing) diabetes or pre-diabetes in a patient or an individual comprising:

(a) practicing a method of the invention, wherein the paracrine polypeptide or peptide comprises or consists of a urocortin-2 (UCn-2); and (b) administering a urocortin-2 (UCn-2) peptide or polypeptide, or a nucleic acid, gene, message or transcript encoding a urocortin-2 (UCn-2) to an individual or patient in need thereof, wherein optionally the urocortin-2 (UCn-2) peptide or polypeptide is an isolated, a recombinant, a synthetic and/or a peptidomimetic peptide or polypeptide or variant thereof, thereby treating, ameliorating or protecting (preventing) the diabetes or pre-diabetes in the patient or individual.

In alternative embodiments, the invention provides methods of treating, ameliorating or protecting (preventing) obesity in a patient or an individual comprising:

(a) practicing a method of the invention, wherein the paracrine polypeptide or peptide comprises or consists of a urocortin-2 (UCn-2); and (b) administering a urocortin-2 (UCn-2) peptide or polypeptide, or a nucleic acid, gene, message or transcript encoding a urocortin-2 (UCn-2) to an individual or patient in need thereof, wherein optionally the urocortin-2 (UCn-2) peptide or polypeptide is an isolated, a recombinant, a synthetic and/or a peptidomimetic peptide or polypeptide or variant thereof, thereby treating, ameliorating or protecting (preventing) the obesity in the patient or individual.

In alternative embodiments, the invention provides methods of suppressing weight gain, or suppressing the appetite, or stimulating or initiating weight loss, in a patient or an individual comprising:

(a) practicing a method of the invention, wherein the paracrine polypeptide or peptide comprises or consists of a urocortin-2 (UCn-2); and (b) administering a urocortin-2 (UCn-2) peptide or polypeptide, or a nucleic acid, gene, message or transcript encoding a urocortin-2 (UCn-2) to an individual or patient in need thereof, wherein optionally the urocortin-2 (UCn-2) peptide or polypeptide is an isolated, a recombinant, a synthetic and/or a peptidomimetic peptide or polypeptide or variant thereof, thereby suppressing weight gain, or suppressing the appetite, or stimulating or initiating weight loss, in the patient or individual.

In alternative embodiments, the urocortin-2 (UCn-2) peptide or polypeptide is formulated in or as a vesicle, liposome, nanoparticle or nanolipid particle (NLP), or is formulated for: oral administration, intramuscular (IM) injection, intravenous (IV) injection, subcutaneous (SC) or intradermal injection, intrathecal injection, intra-arterial (IA) injection, intracoronary injection, inhalation, or administration by aerosol.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

FIG. 4A illustrates a photomicrograph of the uninjected side, FIG. 4B illustrates a photomicrograph of the injected side, FIG. 4C illustrates a photomicrograph of an inset of the injected side; and FIG. 4D illustrates Table 4, which summarizes data from the echocardiography measuring the effects of Skeletal Muscle IGFI Expression in CHF, as described in Example 2, below.

FIG. 6A graphically illustrates data from TUNEL staining that indicated that activation of IGFI expression (IGF-On) was associated with reduced cardiac myocyte apoptosis; FIG. 6B illustrates picrosirius red-stained sections of the uninfarcted intraventricular septum from IGF-Off and IGF-On rats that showed reduced cardiac fibrosis, and collagen fractional area was reduced; and FIG. 6C graphically illustrates this data from the IGF-Off and IGF-On rats, as described in Example 2, below.

FIG. 12A graphically illustrates a time course of UCn2 mRNA expression in liver after IV administration of the exemplary AAV8.CBA.UCn2 construct; and FIG. 12B graphically illustrates data showing UCn2 mRNA expression in LV 6 weeks after AAV8.CBA.UCn2 IV administration, as described in Example 3, below.

FIG. 13A graphically illustrates data showing UCn2 gene transfer increased LV contractile function; FIG. 13B graphically illustrates data showing—dP/dt also was reduced, indicating enhanced LV relaxation, as described in Example 3, below.

FIG. 14A illustrates the study protocol; and FIG. 14B and FIG. 14C illustrate data showing the effects of UCn2 transfer on the failing heart, as described in Example 3, below.

FIG. 16A graphically illustrates that UCn2 gene transfer increased the rate of $Ca^{2+}$ decline; 16B graphically illustrates that time-to-$Ca^{2+}$ transient decay was shortened in cardiac myocytes from mice that had received UCN2 gene transfer 4 w prior, as described in Example 3, below.

FIG. 17A illustrates that UCn2 preserves morphological normality 24 hr after $NaN_3$ treatment; FIG. 17B graphically illustrates that UCn2 reduced LDH release after $NaN_3$ treatment, as described in Example 3, below.

FIG. 19A illustrates that a small reduction in fasting blood glucose was seen in the UCn2 group: FIG. 19B illustrates results indicating that UCn2 gene transfer promotes glucose utilization and protects against diet-induced hyperglycemia, as described in Example 3, below.

FIG. 26 illustrates Table 5.

Like reference symbols in the various drawings indicate like elements.

DETAILED DESCRIPTION

Figure 1:
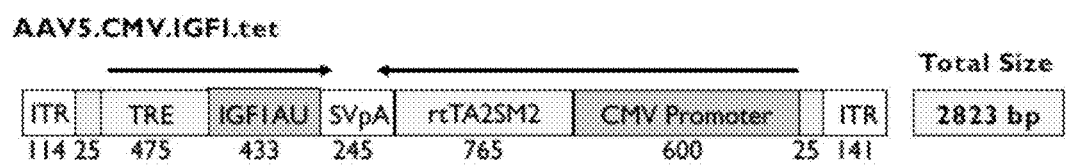
FIG. 1 illustrates an exemplary construct of the invention comprising AAV5 encoding IGF1, as described in Example 2, below.

The invention provides compositions and in vivo and ex vivo methods comprising administration of paracrine-encoding nucleic acids, genes, transcripts or messages to treat, ameliorate or protect (as a prophylaxis) individuals against diseases, infections or conditions responsive to increased paracrine levels in vivo. In alternative embodiments, the invention provides compositions and methods for the in vivo or in situ delivery and/or in vivo expression of, and controlled expression of, any paracrine polypeptide or peptide, e.g., a mammalian cardiotonic peptide, a Serelaxin, a Relaxin-2, a Urocortin-2, a Urocortin-1, a Urocortin-3, a Brain Natriuretic Peptide, a Prostacyclin Synthase, a Growth Hormone, an Insulin-like Growth Factor-1, or any combination thereof; or, a human cardiotonic peptide, a Serelaxin, a Relaxin-2, a Urocortin-2, a Urocortin-1, a Urocortin-3, a Brain Natriuretic Peptide, a Prostacyclin Synthase, a Growth Hormone, an Insulin-like Growth Factor-1, or any combination thereof.

In alternative embodiments, the invention provides compositions and methods for the delivery and controlled expression of a paracrine-encoding nucleic acid or gene, or an expression vehicle (e.g., vector, recombinant virus, and the like) comprising (having contained therein) a paracrine-encoding nucleic acid or gene, that results in a paracrine protein being released into the bloodstream or general circulation where it can have a beneficial effect on in the body, e.g., such as the heart in the case of treating cardiovascular disease, or the lungs or kidneys, or other targets.

In alternative embodiments, the invention provides expression vehicles, vectors, recombinant viruses and the like for in vivo expression of a paracrine-encoding nucleic acid or gene to practice the methods of this invention. In alternative embodiments, the expression vehicles, vectors, recombinant viruses and the like expressing the paracrine-encoding nucleic acid or gene can be delivered by intramuscular (IM) injection, by intravenous (IV) injection, by subcutaneous injection, by inhalation, by a biolistic particle delivery system (e.g., a so-called "gene gun"), and the like, e.g., as an outpatient, e.g., during an office visit.

In alternative embodiments, this "peripheral" mode of delivery, e.g., expression vehicles, vectors, recombinant viruses and the like injected IM or IV, can circumvent problems encountered when genes or nucleic acids are expressed directly in an organ (e.g., the heart, lung or kidney) itself. Sustained secretion of a desired paracrine protein(s) in the bloodstream or general circulation also circumvents the difficulties and expense of administering proteins by infusion, which can be particularly problematic for many proteins which exhibit very short half lives in the body, as summarized in Table 1, below:

TABLE I

Peptide IV Infusion vs Gene Transfer

| Feature | IV Infusion | Gene Transfer |
|---|---|---|
| Requires Hospitalization | Most Often | No |
| Indwelling Catheters | Often | No |
| Infection Risk | High | No |
| Thrombosis Risk | High | No |
| Expense | High | Low |
| Ease of Use | Low | High |
| "Mobility" of Therapy | Low | High |
| Efficacy in CHF | Yes | Untested |
| Dosage Regulation | Tight | Via Reg Expression |

"Mobility" refers to ease of using when away from home (travelling, etc.);
Reg. Regulated (the patient takes an oral agent in a dose that provides the desired level of transgene expression)

In alternative embodiments, the invention provides methods for being able to turn on and turn off paracrine-expressing nucleic acid or gene expression easily and efficiently for tailored treatments and insurance of optimal safety.

In alternative embodiments, the paracrine protein or proteins expressed by the paracrine-expressing nucleic acid(s) or gene(s) have a beneficial or favorable effects (e.g., therapeutic or prophylactic) on a tissue or an organ, e.g., the heart, blood vessels, lungs, kidneys, or other targets, even though secreted into the blood or general circulation at a distance (e.g., anatomically remote) from their site or sites of action.

In an exemplary embodiment of the invention, a paracrine-expressing nucleic acid or gene encoding Urocortin-2 is used, but other paracrine-expressing nucleic acids or genes can be used to practice methods of this invention, including but not limited to, e.g., for treating congestive heart failure (CHF) or pulmonary hypertension: Urocortin-1 and Urocortin-3, Brain Natriuretic Peptide (for CHF), Prostacyclin Synthase (for pulmonary hypertension), Growth Hormone, and/or Insulin-like Growth Factor-1, or any combination thereof.

In alternative embodiments the invention provides applications, and compositions and methods, for a regulated expression system providing for controlled expression of a paracrine-type gene to treat a heart or lung disease, e.g., congestive heart failure (CHF) or pulmonary hypertension.

For example, in alternative embodiments a recombinant virus (e.g., a long-term virus or viral vector), or a vector, or an expression vector, and the like, can be injected, e.g., in a systemic vein (e.g., IV), or by intramuscular (IM) injection, by inhalation, or by a biolistic particle delivery system (e.g., a so-called "gene gun"), e.g., as an outpatient, e.g., in a physician's office. In alternative embodiments, days or weeks later (e.g., four weeks later), the individual, patient or subject is administered (e.g., inhales, is injected or swallows), a chemical or pharmaceutical that induces expression of the paracrine-expressing nucleic acids or genes; for example, an oral antibiotic (e.g., doxycycline or rapamycin) is administered once daily (or more or less often), which will activate the expression of the gene. In alternative embodiments, after the "activation", or inducement of expression (e.g., by an inducible promoter) of the nucleic acid or gene, a paracrine protein is synthesized and released into the subject's circulation (e.g., into the blood), and subsequently has favorable physiological effects, e.g., therapeutic or prophylactic, that benefit the individual or patient (e.g., benefit heart, kidney or lung function), depending on the paracrine protein or proteins expressed. When the physician or subject desires discontinuation of the treatment, the subject simply stops taking the activating chemical or pharmaceutical, e.g., antibiotic.

The inventors have used an AAV vector encoding Urocortin-2 and administered the vector to mice using intravenous delivery. The results showed: 1) a 17-fold increase in serum levels of the transgene 4-6 weeks after intravenous delivery of the vector; 2) pronounced favorable effects on cardiac contractile function (systolic function); and 3) pronounced favorable effects on cardiac relaxation (diastolic function).

In alternative embodiments, applications of the present invention include: the treatment of severe, low ejection fraction heart failure; the treatment of pulmonary hypertension; the treatment of heart failure with preserved ejection fraction; replacement of current therapies that require hospitalization and sustained intravenous infusions of vasoactive peptides for the treatment of pulmonary hypertension and heart failure; and, the treatment of other conditions in which controlled expression of a paracrine-type gene can be used to promote favorable effects at a distance in the body.

Generating and Manipulating Nucleic Acids

In alternative embodiments, to practice the methods of the invention, the invention provides isolated, synthetic and/or recombinant nucleic acids or genes encoding paracrine polypeptides. In alternative embodiments, to practice the methods of the invention, the invention provides paracrine-expressing nucleic acids or genes in recombinant form in an (e.g., spliced into) an expression vehicle for in vivo expression, e.g., in a vector or a recombinant virus. In other alternative embodiments, the invention provides, e.g., isolated, synthetic and/or recombinant nucleic acids encoding inhibitory nucleic acids (e.g., siRNA, microRNA, antisense, ribozyme) that can inhibit the expression of genes or messages (mRNAs) that inhibit the expression of the desired paracrine gene.

In alternative embodiments, nucleic acids of the invention are made, isolated and/or manipulated by, e.g., cloning and expression of cDNA libraries, amplification of message or genomic DNA by PCR, and the like. The nucleic acids and genes used to practice this invention, including DNA, RNA, iRNA, antisense nucleic acid, cDNA, genomic DNA, vectors, viruses or hybrids thereof, can be isolated from a variety of sources, genetically engineered, amplified, and/or expressed/generated recombinantly. Recombinant polypeptides (e.g., paracrine chimeric proteins used to practice this invention) generated from these nucleic acids can be individually isolated or cloned and tested for a desired activity. Any recombinant expression system or gene therapy delivery vehicle can be used, including e.g., viral (e.g., AAV constructs or hybrids) bacterial, fungal, mammalian, yeast, insect or plant cell expression systems or expression vehicles.

Alternatively, nucleic acids used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In alternative embodiments, to practice the methods of the invention, paracrine fusion proteins and nucleic acids encoding them are used. Any paracrine polypeptide can be used to practice this invention, e.g., a Urocortin-1, a Urocortin-2, a Urocortin-3, a Brain Natriuretic Peptide, a Prostacyclin Synthase, a Growth Hormone, an Insulin-like Growth Factor-1 protein. In alternative embodiments, the paracrine protein can be fused to a heterologous peptide or polypeptide, such as a peptide for targeting the polypeptide to a desired cell type, such a cardiac myocytes, or a lung cell.

In alternative embodiments, a heterologous peptide or polypeptide joined or fused to a protein used to practice this invention can be an N-terminal identification peptide which imparts a desired characteristic, such as fluorescent detection, increased stability and/or simplified purification. Peptides and polypeptides used to practice this invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Nucleic acids or nucleic acid sequences used to practice this invention can be an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin. Compounds use to practice this invention include "nucleic acids" or "nucleic acid sequences" including oligonucleotide, nucleotide, polynucleotide, or any fragment of any of these; and include DNA or RNA (e.g., mRNA, rRNA, tRNA, iRNA) of genomic or synthetic origin which may be single-stranded or double-stranded; and can be a sense or antisense strand, or a peptide nucleic acid (PNA), or any DNA-like or RNA-like material, natural or synthetic in origin, including, e.g., iRNA, ribonucleoproteins (e.g., e.g., double stranded iRNAs, e.g., iRNPs). Compounds use to practice this invention include nucleic acids, i.e., oligonucleotides, containing known analogues of natural nucleotides. Compounds use to practice this invention include nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. Compounds use to practice this invention include "oligonucleotides" including a single stranded polydeoxynucleotide or two complementary polydeoxynucleotide strands that may be chemically synthesized. Compounds use to practice this invention include synthetic oligonucleotides having no 5' phosphate, and thus will not ligate to another oligonucleotide without adding a phosphate with an ATP in the presence of a kinase. A synthetic oligonucleotide can ligate to a fragment that has not been dephosphorylated.

In alternative aspects, compounds used to practice this invention include genes or any segment of DNA involved in producing a paracrine polypeptide (e.g., a Urocortin-1, a Urocortin-2, a Urocortin-3, a Brain Natriuretic Peptide, a Prostacyclin Synthase, a Growth Hormone, an Insulin-like Growth Factor-1 protein); it can include regions preceding and following the coding region (leader and trailer) as well as, where applicable, intervening sequences (introns) between individual coding segments (exons). "Operably linked" can refer to a functional relationship between two or more nucleic acid (e.g., DNA) segments. In alternative aspects, it can refer to the functional relationship of transcriptional regulatory sequence to a transcribed sequence. For example, a promoter can be operably linked to a coding sequence, such as a nucleic acid used to practice this invention, if it stimulates or modulates the transcription of the coding sequence in an appropriate host cell or other expression system. In alternative aspects, promoter transcriptional regulatory sequences can be operably linked to a transcribed sequence where they can be physically contiguous to the transcribed sequence, i.e., they can be cis-acting. In alternative aspects, transcriptional regulatory sequences, such as enhancers, need not be physically contiguous or located in close proximity to the coding sequences whose transcription they enhance.

In alternative aspects, the invention comprises use of "expression cassettes" comprising a nucleotide sequences used to practice this invention, which can be capable of affecting expression of the nucleic acid, e.g., a structural gene or a transcript (e.g., encoding a paracrine protein) in a host compatible with such sequences. Expression cassettes can include at least a promoter operably linked with the polypeptide coding sequence or inhibitory sequence; and, in one aspect, with other sequences, e.g., transcription termination signals. Additional factors necessary or helpful in effecting expression may also be used, e.g., enhancers.

In alternative aspects, expression cassettes used to practice this invention also include plasmids, expression vectors, recombinant viruses, any form of recombinant "naked DNA" vector, and the like. In alternative aspects, a "vector" used to practice this invention can comprise a nucleic acid that can infect, transfect, transiently or permanently transduce a cell. In alternative aspects, a vector used to practice this invention can be a naked nucleic acid, or a nucleic acid complexed with protein or lipid. In alternative aspects, vectors used to practice this invention can comprise viral or bacterial nucleic acids and/or proteins, and/or membranes (e.g., a cell membrane, a viral lipid envelope, etc.). In alternative aspects, vectors used to practice this invention can include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and can include both the expression and non-expression plasmids. In alternative aspects, the vector used to practice this invention can be stably replicated by the cells during mitosis as an autonomous structure, or can be incorporated within the host's genome.

In alternative aspects, "promoters" used to practice this invention include all sequences capable of driving transcription of a coding sequence in a cell, e.g., a mammalian cell such as a heart, lung, muscle, nerve or brain cell. Thus, promoters used in the constructs of the invention include cis-acting transcriptional control elements and regulatory sequences that are involved in regulating or modulating the timing and/or rate of transcription of a gene. For example, a promoter used to practice this invention can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription.

In alternative embodiments, "constitutive" promoters used to practice this invention can be those that drive expression continuously under most environmental conditions and states of development or cell differentiation. In alternative embodiments, "Inducible" or "regulatable" promoters used to practice this invention can direct expression of the nucleic acid of the invention under the influence of environmental conditions, administered chemical agents, or developmental conditions.

Gene Therapy and Gene Delivery Vehicles

In alternative embodiments, methods of the invention comprise use of nucleic acid (e.g., gene or polypeptide encoding nucleic acid) delivery systems to deliver a payload of a paracrine-encoding nucleic acid or gene, or a paracrine polypeptide-expressing nucleic acid, transcript or message, to a cell or cells in vitro, ex vivo, or in vivo, e.g., as gene therapy delivery vehicles.

In alternative embodiments, expression vehicle, vector, recombinant virus, or equivalents used to practice methods of the invention are or comprise: an adeno-associated virus (AAV), a lentiviral vector or an adenovirus vector; an AAV serotype AAV5, AAV6, AAV8 or AAV9; a rhesus-derived AAV, or the rhesus-derived AAV AAVrh.10hCLN2; an organ-tropic AAV, or a cardiotropic AAV, or a cardiotropic AAVM41 mutant; and/or an AAV capsid mutant or AAV hybrid serotype. In alternative embodiments, the AAV is engineered to increase efficiency in targeting a specific cell type that is non-permissive to a wild type (wt) AAV and/or to improve efficacy in infecting only a cell type of interest. In alternative embodiments, the hybrid AAV is retargeted or engineered as a hybrid serotype by one or more modifications comprising: 1) a transcapsidation, 2) adsorption of a bi-specific antibody to a capsid surface, 3) engineering a mosaic capsid, and/or 4) engineering a chimeric capsid. It is well known in the art how to engineer an adeno-associated virus (AAV) capsid in order to increase efficiency in targeting specific cell types that are non-permissive to wild type (wt) viruses and to improve efficacy in infecting only the cell type of interest; see e.g., Wu et al., Mol. Ther. 2006 September; 14(3):316-27. Epub 2006 Jul. 7; Choi, et al., Curr. Gene Ther. 2005 June; 5(3):299-310.

Use of any AAV serotype is considered within the scope of the present invention. In some embodiments, a rAAV vector is a vector derived from an AAV serotype, including without limitation, AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV ITRs or the like. In some embodiments, the nucleic acid in the AAV comprises an ITR of AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV or the like.

For example, the rhesus-derived AAV AAVrh.10hCLN2 or equivalents thereof can be used, wherein the rhesus-derived AAV may not be inhibited by any pre-existing immunity in a human; see e.g., Sondhi, et al., Hum Gene Ther. Methods. 2012 October; 23(5):324-35, Epub 2012 Nov. 6; Sondhi, et al., Hum Gene Ther. Methods. 2012 Oct. 17; teaching that direct administration of AAVrh.10hCLN2 to the CNS of rats and non-human primates at doses scalable to humans has an acceptable safety profile and mediates significant payload expression in the CNS.

Also, for example, AAV vectors specifically designed for cardiac gene transfer (a cardiotropic AAV) can be used, e.g., the AAVM41 mutant having improved transduction efficiency and specificity in the myocardium, see, e.g., Yang, et al. Virol J. 2013 Feb. 11; 10(1):50.

Because adeno-associated viruses (AAVs) are common infective agents of primates, and as such, healthy primates carry a large pool of AAV-specific neutralizing antibodies (NAbs) which inhibit AAV-mediated gene transfer therapeutic strategies, the methods of the invention comprise screening of patient candidates for AAV-specific NAbs prior to treatment, especially with the frequently used AAV8 capsid component, to facilitate individualized treatment design and enhance therapeutic efficacy; see, e.g., Sun, et al., J. Immunol. Methods. 2013 Jan. 31; 387(1-2):114-20, Epub 2012 Oct. 11.

Kits and Instructions

The invention provides kits comprising compositions and methods of the invention, including instructions for use thereof. As such, kits, cells, expression vehicles (e.g., recombinant viruses, vectors) and the like can also be provided.

For example, in alternative embodiments, the invention provides kits comprising compositions used to practice this invention, e.g., comprising a urocortin-2 (UCn-2) peptide or polypeptide; or a paracrine-encoding nucleic acid, (b) a liquid or aqueous formulation of the invention, or (c) the vesicle, liposome, nanoparticle or nanolipid particle of the invention. In one aspect, the kit further comprising instructions for practicing any methods of the invention, e.g., in vitro or ex vivo methods for increasing a desired paracrine level in the bloodstream, or for protecting a cell, e.g., a cardiac or lung cell; or for treating, preventing or ameliorating diabetes or pre-diabetes.

Formulations

In alternative embodiments, the invention provides compositions and methods for use in increasing paracrine levels in vivo. In alternative embodiments, these compositions comprise paracrine-encoding nucleic acids formulated for these purposes, e.g., expression vehicles or paracrine-encoding nucleic acids formulated in a buffer, in a saline solution, in a powder, an emulsion, in a vesicle, in a liposome, in a nanoparticle, in a nanolipoparticle and the like.

In alternative embodiments, the invention provides methods comprising administration of urocortin-2 (UCn-2) peptides or polypeptides, or UCn-2-encoding nucleic acids, to treat, ameliorate or prevent a diabetes (including Type 1 and Type 2, or adult onset diabetes) or pre-diabetes, or obesity or excess weight; or to stimulate weight loss, or to act as an appetite suppressant. Accordingly, the invention provides the appropriate formulations and dosages of urocortin-2 (UCn-2) peptides or polypeptides, or UCn-2-encoding nucleic acids, for same.

In alternative embodiments, the compositions (including formulations of urocortin-2 (UCn-2) peptides or polypeptides, or paracrine-encoding (e.g., UCn-2-encoding) nucleic acids, can be formulated in any way and can be applied in a variety of concentrations and forms depending on the desired in vitro, in vivo or ex vivo conditions, including a desired in vivo or ex vivo method of administration and the like. Details on techniques for in vitro, in vivo or ex vivo formulations and administrations are well described in the scientific and patent literature.

Formulations and/or carriers of the paracrine-encoding nucleic acids, or urocortin-2 (UCn-2) peptides or polypeptides, used to practice this invention are well known in the art. Formulations and/or carriers used to practice this invention can be in forms such as tablets, pills, powders, capsules, liquids, gels, syrups, slurries, suspensions, etc., suitable for in vivo or ex vivo applications.

In alternative embodiments, paracrine-encoding nucleic acids, or urocortin-2 (UCn-2) peptides or polypeptides, used to practice this invention can be in admixture with an aqueous and/or buffer solution or as an aqueous and/or buffered suspension, e.g., including a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate. Formulations can be adjusted for osmolarity, e.g., by use of an appropriate buffer.

In practicing this invention, the compounds (e.g., formulations) of the invention can comprise a solution of paracrine-encoding nucleic acids or genes, or urocortin-2 (UCn-2) peptides or polypeptides, dissolved in a pharmaceutically acceptable carrier, e.g., acceptable vehicles and solvents that can be employed include water and Ringer's solution, an isotonic sodium chloride. In addition, sterile fixed oils can be employed as a solvent or suspending medium. For this purpose any fixed oil can be employed including synthetic mono- or diglycerides, or fatty acids such as oleic acid. In one embodiment, solutions and formulations used to practice the invention are sterile and can be manufactured to be generally free of undesirable matter. In one embodiment, these solutions and formulations are sterilized by conventional, well known sterilization techniques.

The solutions and formulations used to practice the invention can comprise auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent (e.g., paracrine-encoding nucleic acids or genes) in these formulations can vary widely, and can be selected primarily based on fluid volumes, viscosities and the like, in accordance with the particular mode of in vivo or ex vivo administration selected and the desired results, e.g., increasing in vivo paracrine expression.

The solutions and formulations used to practice the invention can be lyophilized; for example, the invention provides a stable lyophilized formulation comprising paracrine-encoding nucleic acids or genes, or urocortin-2 (UCn-2) peptides or polypeptides. In one aspect, this formulation is made by lyophilizing a solution comprising a paracrine-encoding nucleic acid or gene, or urocortin-2 (UCn-2) peptides or polypeptides, and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations of the invention can be delivered by the use of liposomes (see also discussion, below). By using liposomes, particularly where the liposome surface carries ligands specific for target cells, or are otherwise preferentially directed to a specific tissue or organ type, one can focus the delivery of the active agent into a target cells in an in vivo or ex vivo application.

Nanoparticles, Nanolipoparticles and Liposomes

The invention also provides nanoparticles, nanolipoparticles, vesicles and liposomal membranes comprising compounds (e.g., paracrine-encoding nucleic acids or genes, or urocortin-2 (UCn-2) peptides or polypeptides) used to practice the methods of this invention, e.g., to deliver paracrine-encoding nucleic acids or genes, or urocortin-2 (UCn-2) peptides or polypeptides, to an individual, a patient or mammalian cells in vivo or ex vivo. In alternative embodiments, these compositions are designed to target specific molecules, including biologic molecules, such as polypeptides, including cell surface polypeptides, e.g., for targeting a desired cell type, e.g., a mammalian cardiac cell, a kidney cell, a lung cell, a nerve cell and the like.

The invention provides multilayered liposomes comprising compounds used to practice this invention, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, e.g., to entrap a paracrine-encoding nucleic acid or gene.

Liposomes can be made using any method, e.g., as described in Park, et al., U.S. Pat. Pub. No. 20070042031, including method of producing a liposome by encapsulating an active agent (e.g., paracrine-encoding nucleic acids or genes, or urocortin-2 (UCn-2) peptides or polypeptides), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice this invention comprise a substituted ammonium and/or polyanions, e.g., for targeting delivery of a compound (e.g., paracrine-encoding nucleic acids or genes) used to practice this invention to a desired cell type, as described e.g., in U.S. Pat. Pub. No. 20070110798.

The invention also provides nanoparticles comprising compounds (e.g., paracrine-encoding nucleic acids or genes, or urocortin-2 (UCn-2) peptides or polypeptides) used to practice this invention in the form of active agent-containing nanoparticles (e.g., a secondary nanoparticle), as described, e.g., in U.S. Pat. Pub. No. 20070077286. In one embodiment, the invention provides nanoparticles comprising a fat-soluble active agent of this invention or a fat-solubilized water-soluble active agent to act with a bivalent or trivalent metal salt.

In one embodiment, solid lipid suspensions can be used to formulate and to deliver paracrine-encoding nucleic acids or genes, or urocortin-2 (UCn-2) peptides or polypeptides, used to practice the invention to a patient, an individual, or mammalian cell in vivo or ex vivo, as described, e.g., in U.S. Pat. Pub. No. 20050136121.

Delivery Vehicles

In alternative embodiments, any delivery vehicle can be used to practice the methods or compositions of this invention, e.g., to deliver paracrine-encoding nucleic acids or genes, or urocortin-2 (UCn-2) peptides or polypeptides, to practice the methods of the invention in vivo or ex vivo. For example, delivery vehicles comprising polycations, cationic polymers and/or cationic peptides, such as polyethyleneimine derivatives, can be used e.g. as described, e.g., in U.S. Pat. Pub. No. 20060083737.

In one embodiment, a dried polypeptide-surfactant complex is used to formulate a composition of the invention, wherein a surfactant is associated with a nucleic acid via a non-covalent bond e.g. as described, e.g., in U.S. Pat. Pub. No. 20040151766.

In one embodiment, a nucleic acid or polypeptide used to practice this invention can be applied to cells as polymeric hydrogels or water-soluble copolymers, e.g., as described in U.S. Pat. No. 7,413,739; for example, a nucleic acid or protein can be polymerized through a reaction between a strong nucleophile and a conjugated unsaturated bond or a conjugated unsaturated group, by nucleophilic addition, wherein each precursor component comprises at least two strong nucleophiles or at least two conjugated unsaturated bonds or conjugated unsaturated groups.

In one embodiment, a nucleic acid or protein is applied to cells using vehicles with cell membrane-permeant peptide conjugates, e.g., as described in U.S. Pat. Nos. 7,306,783; 6,589,503. In one aspect, the nucleic acid itself is conjugated to a cell membrane-permeant peptide. In one embodiment, a nucleic acid, protein, and/or the delivery vehicle are conjugated to a transport-mediating peptide, e.g., as described in U.S. Pat. No. 5,846,743, describing transport-mediating peptides that are highly basic and bind to poly-phosphoinositides.

In one embodiment, electro-permeabilization is used as a primary or adjunctive means to deliver a paracrine-encoding nucleic acids or genes to a cell, e.g., using any electroporation system as described e.g. in U.S. Pat. Nos. 7,109,034; 6,261,815; 5,874,268.

Products of Manufacture, Implants and Artificial Organs

The invention also provides products of manufacture comprising cells of the invention (e.g., cells modified to express paracrine proteins, or urocortin-2 (UCn-2) peptides or polypeptides, to practice the methods of the invention), and use of cells made by methods of this invention, including for example implants and artificial organs, bioreactor systems, cell culture systems, plates, dishes, tubes, bottles and flasks comprising cells modified to express paracrine proteins to practice the methods of the invention. Any implant, artificial organ, bioreactor systems, cell culture system, cell culture plate, dish (e.g., petri dish), cell culture tube and/or cell culture flask (e.g., a roller bottle) can be used to practice this invention.

In alternative embodiments the invention provides a bioreactor, implant, stent, artificial organ or similar device comprising cells modified to express paracrine proteins to practice the methods of the invention; for example, including implants as described in U.S. Pat. Nos. 7,388,042; 7,381,418; 7,379,765; 7,361,332; 7,351,423; 6,886,568; 5,270,192; and U.S. Pat. App. Pub. Nos. 20040127987; 20080119909 (describing auricular implants); 20080118549 (describing ocular implants); 20080020015 (describing a bioactive wound dressing); 20070254005 (describing heart valve bio-prostheses, vascular grafts, meniscus implants); 20070059335; 20060128015 (describing liver implants).

Implanting Cells In Vivo

In alternative embodiments, the methods of the invention also comprise implanting or engrafting cells, e.g., cardiac, lung or kidney cells, comprising or expressing paracrine-encoding nucleic acids or genes, or urocortin-2 (UCn-2) peptides or polypeptides, used to practice the invention; and in one aspect, methods of the invention comprise implanting or engrafting the paracrine-encoding nucleic acids or genes (or cells expressing them), or urocortin-2 (UCn-2) peptides or polypeptides, in a vessel, tissue or organ ex vivo or in vivo, or implanting or engrafting the re-programmed differentiated cell in an individual in need thereof.

Cells can be removed from an individual, treated using the compositions and/or methods of this invention, and reinserted (e.g., injected or engrafted) into a tissue, organ or into the individual, using any known technique or protocol. For example, de-differentiated re-programmed cells, or re-programmed differentiated cells, can be re-implanted (e.g., injected or engrafted) using microspheres e.g., as described in U.S. Pat. No. 7,442,389; e.g., in one aspect, the cell carrier comprises a bulking agent comprising round and smooth polymethylmethacrylate microparticles preloaded within a mixing and delivery system and an autologous carrier comprising these cells. In another embodiment, the cells are readministered to a tissue, an organ and/or an individual in need thereof in a biocompatible crosslinked matrix, as described e.g., in U.S. Pat. App. Pub. No. 20050027070.

In another embodiment, the cells of the invention (e.g., cells made by practicing the methods of this invention) are readministered (e.g., injected or engrafted) to a tissue, an organ and/or an individual in need thereof within, or protected by, a biocompatible, nonimmunogenic coating, e.g., as on the surface of a synthetic implant, e.g., as described in U.S. Pat. No. 6,969,400, describing e.g., a protocol where a cAMP-incompetent AC can be conjugated to a polyethylene glycol that has been modified to contain multiple nucleophilic groups, such as primary amino or thiol group.

In one embodiment, the cells of the invention (e.g., cells made by practicing the methods of this invention) are readministered (e.g., injected or engrafted) to a tissue, an organ and/or an individual in need thereof using grafting methods as described e.g. by U.S. Pat. Nos. 7,442,390; 5,733,542.

Any method for delivering polypeptides, nucleic acids and/or cells to a tissue or organ (e.g., a lung, kidney, heart) can be used, and these protocols are well known in the art, e.g., as described in U.S. Pat. No. 7,514,401, describing e.g., using intracoronary (IC), intravenous (IV), and/or local delivery (myocardial injection) of polypeptides, nucleic acids and/or cells to a heart in situ. For example, in alternative embodiments, aerosol drug particles into the lungs and into the bloodstream, gene therapy, continuous infusions, repeated injections and/or sustained release polymers can be used for delivering polypeptides, nucleic acids and/or cells to a tissue or organ (e.g., a lung, kidney, heart). In alternative embodiments, nucleic acids and/or cells can be given through a catheter into the coronary arteries or by direct injection into the left atrium or ventricular myocardium via a limited thoracotomy; or delivered into the myocardium via a catheter passed during cardiac catheterization; or delivered into the pericardial space.

In alternative embodiments, nucleic acids or proteins used to practice this invention, or a vector comprising a nucleic acid used to practice the invention (e.g., an AAV, or adenoviral gene therapy vector), or vesicle, liposome, nanoparticle or nanolipid particle (NLP) of the invention, and the like, to a tissue or organ (e.g., a lung, kidney, heart); e.g. as described in U.S. Pat. No. 7,501,486, e.g., polypeptides of the invention comprising an amino acid sequence CRPPR (SEQ ID NO:1), the amino acid sequence CARPAR (SEQ ID NO:2) or a peptidomimetic thereof, or amino acid sequence CPKRPR (SEQ ID NO:3) or a peptidomimetic thereof.

Compositions used to practice this invention can be used in combination with other therapeutic agents, e.g. angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors.

Compositions used to practice this invention can be used for ameliorating or treating any of a variety of cardiopathies and cardiovascular diseases, e.g., cardiopathies and cardiovascular diseases, e.g., coronary artery disease (CAD); atherosclerosis; thrombosis; restenosis; vasculitis including autoimmune and viral vasculitis such as polyarteritis nodosa, Churg-Strass syndrome, Takayasu's arteritis, Kawasaki Disease and Rickettsial vasculitis; atherosclerotic aneurisms; myocardial hypertrophy; congenital heart diseases (CHD); ischemic heart disease and anginas; acquired valvular/endocardial diseases; primary myocardial diseases including myocarditis; arrhythmias; and transplant rejections; metabolic myocardial diseases and myocardiomyopathies such as congestive, hypertrophic and restrictive cardiomyopathies, and/or heart transplants. In alternative embodiments, compositions used to practice this invention, e.g., urocortin-2 (UCn-2) peptides or polypeptides, are used for treating, ameliorating or protecting (preventing) diabetes or pre-diabetes in a patient or an individual; or suppressing weight gain, or suppressing the appetite, or stimulating or initiating weight loss, in a patient or an individual; or treating, ameliorating or protecting (preventing) diabetes in a patient or an individual.

The invention will be further described with reference to the following examples; however, it is to be understood that the invention is not limited to such examples.

EXAMPLES

Example 1

Intravenous Delivery of AAV9 Encoding Urocortin-2 Increases Cardiac Function in Normal Mice This example demonstrates the effectiveness of an exemplary embodiment of the invention: intravenous delivery of AAV9/urocortin-2 (or AAV9/UCn2) provided sustained increases in serum UCn2 and LV contractile function, indicating the effectiveness of this exemplary embodiment of the invention for the treatment of heart failure.

In this study, we developed and tested the relative efficacy of two adeno-associated virus (AAV) serotypes (AAV5 and AAV9) encoding urocortin-2 (UCn-2), which is a vasoactive peptide in the corticotropin-releasing factor family that has protean beneficial effects in animals and patients with heart failure. AAV5.Ucn-2 and AAV9.Ucn-2 ($5 \times 10^{11}$ genome copies, gc) were delivered by intravenous injection (IV). Four weeks (wks) after gene transfer, AAV DNA (qPCR) was elevated in liver (AAV5.UCn2: 2,601,839 copies/m; AAV9.UCn2: 30,121,663 copies/m) and heart (AAV5: 87,635gc/m; AAV9: 300,529 copies/m; and mRNA was similarly elevated compared to endogenous UCn2 (AAV5.Ucn-2: 68±xx-fold; AAV9.Ucn-2: 8,575).

Left ventricular samples showed Ucn2 mRNA elevation only with AAV9.UCn2, which was increased 28 fold over endogenous mRNA. Plasma Ucn-2 was increased (AAV5.UCn2: from 2.7 ng/ml pre to 3.6 ng/ml, p<0.0001; AAV9.UCn2. Finally, associated with increased serum UCn2 levels were increases in LV contractile function.

Example 2

Gene Transfer for the Treatment of Cardiovascular Diseases

This example demonstrates the effectiveness of an exemplary embodiment of the invention in obtaining high yield transgene expression in the heart in a manner that can be easily and safely applied.

In alternative embodiments, the invention provides methods using expression vehicles, e.g., vectors, encoding a paracrine-type transgene. In this embodiment, the transgene acts as a hormone, having cardiac effects after being released to the circulation from a distant site. In alternative embodiments this approach can circumvent the problem of attaining high yield cardiac gene transfer and enable patients to be treated by a systemic injection during an office visit.

We examined multiple AAV serotype vectors and delivery methods, and successfully completed proof-of-concept studies of paracrine gene transfer. Rats with severe dilated CHF underwent skeletal muscle delivery of an adeno-associated virus 5 (AAV5) vector encoding Insulin-like Growth Factor I (IGFI) under tetracycline regulation. This enabled activation of IGFI expression upon adding doxycycline in the rat's water supply. The system provided sustained elevation of serum levels of IGFI and improved function of the failing heart.

In alternative embodiments, a) IGFI gene transfer is used to increase contractile function; b) AAV vectors and promoters are used for intravenous delivery to provide maximal transgene expression with minimal off-target effects; c) regulated transgene expression is used to enable fine-tuning of serum transgene levels, and allow turning expression off and on as needed; d) gene transfer of paracrine-expressing genes, e.g., in a rat model of CHF is used; and e) effective doses of AAV are used, and activators of transgene expression are used following intravenous delivery of the vector, e.g., in normal pigs, using serum paracrine (e.g., IGFI) as an end-point.

In alternative embodiments, IV injection of an AAV vector with regulated expression of selective peptides will, through paracrine-mediated actions, have favorable effects on the failing heart.

Vector Selection. In alternative embodiments adeno-associated virus (AAV) vectors are used, enabling long-term transgene expression superior to adenovirus, while avoiding the potential for insertional mutagenesis associated with lentivirus vectors. Persistent serum elevation of Factor IX, erythropoietin and α1-antitrypsin, have been documented in dogs and nonhuman primates, years after single injections of AAV vectors[1-4] and we have confirmed persistent (>1 year) serum elevation of IGFI after intramuscular injection of AAV5.IGFI-tet in rats in our laboratory.[5] Although recent clinical trials have found that some AAV serotypes incite immune responses,[6,7] newer generation AAV vectors do not appear to have similar problems in preclinical studies in primates.

AAV Serotypes: In alternative embodiments an AAV serotype AAV2 is used, but in some embodiments, "pseudotyped" AAV vectors are preferred. These AAV serotypes, which include AAV5, AAV6, AAV8 and AAV9, are hybrid constructs that include the capsid of AAV2 and unique replication components that confer their specific nomenclature. In alternative embodiments, Intravenous delivery of AAV6, AAV8 and AAV9 is used; these show substantial distribution and transgene expression in heart, liver, skeletal muscle, and elsewhere.

Figure 7:
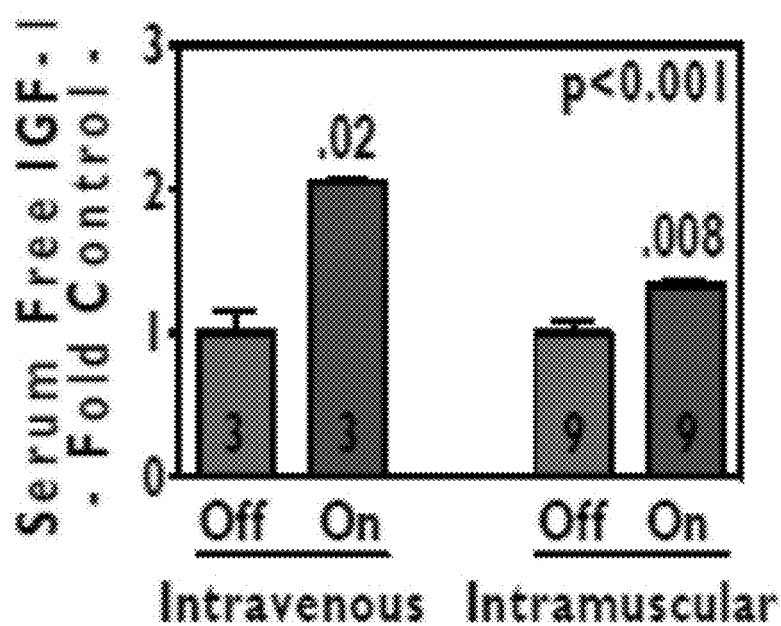
FIG. 7 graphically illustrates that intravenous gave better results than intramuscular administration in increasing serum levels of IGFI when an exemplary when AAV5 construct of the invention was administered: intravenous delivery in mice, intramuscular delivery in rats, as described in Example 2, below.

We found intravenous better than intramuscular AAV5 in increasing serum levels of IGFI, as illustrate in FIG. 7, which graphically show data of free IGFI serum levels 3 months after IV vs. IM AAV5.IGFI.tet gene transfer: Intravenous delivery in mice (n=3, each group) provided a 2-fold increase in serum IGFI after activation of IGFI expression with doxycycline (On); Intramuscular delivery in rats (n=9 each group) provided a >1.3-fold increase in serum IGFI 5 weeks after activation of IGFI expression. P values above bars: within group comparison (t-test, 2 tails). Change in serum IGFI was greater after intravenous delivery of AAV5.IGFI.tet (p<0.001).

Figure 8:
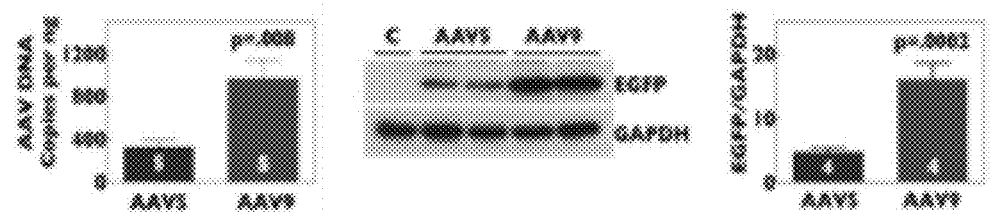
FIG. 8 graphically, and by image, illustrates data showing the relative efficacy of intravenous delivery of exemplary AAV5 and AAV9 constructs of the invention using copy number and transgene expression in liver and heart as endpoints, as described in Example 2, below.
Figure 8:
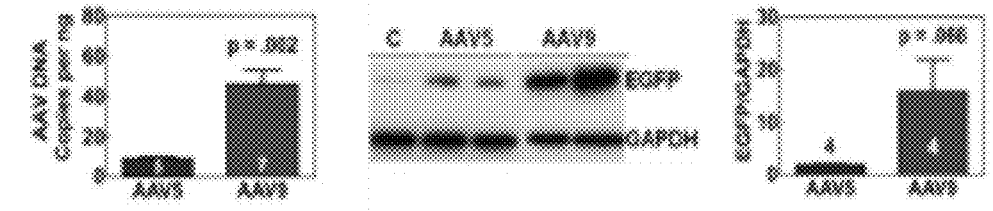
Figure 9:
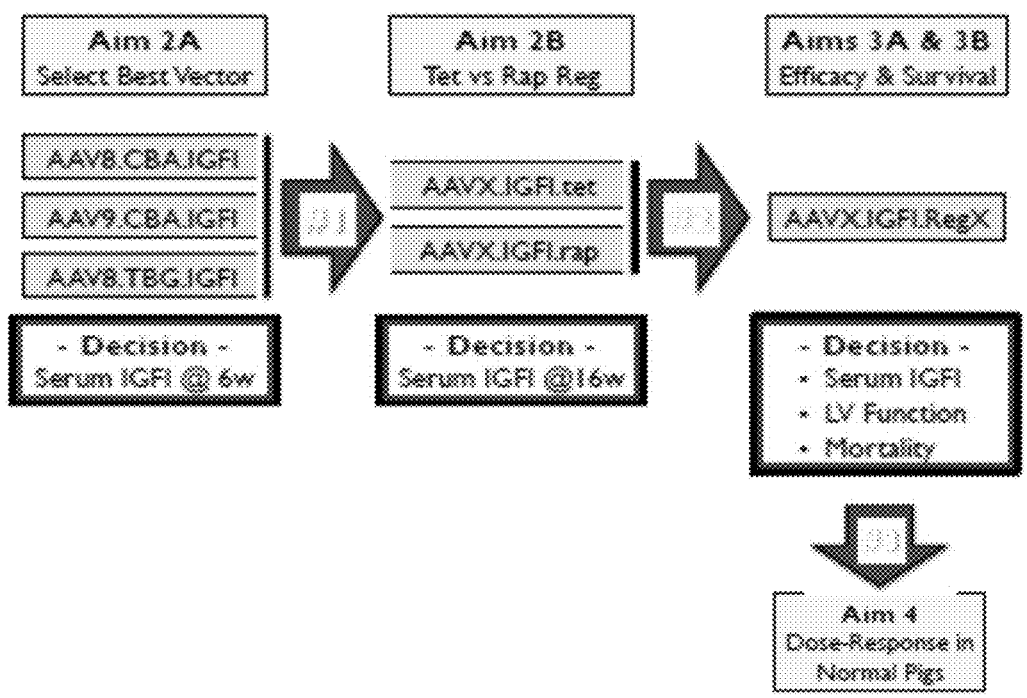
FIG. 9 illustrates an exemplary protocol for determining and testing the most appropriate vector to use for a desired or a particular indication when practicing a method of the invention, as discussed in Example 2, below.

When given intravenously, AAV9 was superior to AAV5 in terms of transgene expression in liver and heart, as illustrate in FIG. 8 graphically, and by image, illustrates data showing the relative efficacy of intravenous delivery of exemplary AAV5 and AAV9 constructs of the invention using copy number and transgene expression in liver and heart as endpoints, as illustrated in FIG. 8.

In alternative embodiments, AAV8, like AAV9, provides generalized expression, but provides a higher proportion in liver than other organs, a property that, in combination with a liver-specific promoter, we propose to exploit.

In alternative embodiments, self-complementary AAV vectors (scAAV) vectors are used; they can provide higher transgene expression than their single stranded (ssAAV) analogs.[8] Transgene expression using the ssAAV vectors (insert capacity 4.7 kb) is delayed 4-6 w until the complementary DNA strand is synthesized. By encoding for the complementary DNA strand within the vector, scAAV (insert capacity 3.3 kb), enables transgene expression in 2 w and results in higher transgene expression vs its ssAAV analog.[8]

Only one regulated expression vector (AAV8.TBG.IGFI.tet) may be amenable to scAAV construction, the others are too large, as illustrated in FIG. 10. However, if this vector is selected for the pig studies, ssAAV can be used to provide better yield for manufacturing the large amounts required. The scAAV analog can be used for human use, taking advantage of superior expression, enabling reduced dose requirements, and improving safety in the clinical trials.

Promoter vs Target Tissue. In alternative embodiments, the promoter selected for transgene expression in AAV vectors has some tissue-dependence. In alternative embodiments, promoters used to practice the invention include: chicken β-actin (CBA); thyroid hormone-binding globulin (TBG, liver-specific); and Rous Sarcoma Virus (RSV) promoters. In this regard, CMV has consistently been shown to be a superior promoter in skeletal and cardiac muscle. Recent studies indicate that the CMV promoter is susceptible to methylation in liver, which eventually shuts off transgene expression. Losing liver expression would reduce serum levels of transgene—we therefore have elected not to use the CMV promoter, selecting instead similarly robust promoters less susceptible to methylation: chicken β-actin (CBA); thyroid hormone-binding globulin (TBG, liver-specific); and Rous Sarcoma Virus (RSV) promoters, as illustrated in FIG. 10.

Regulated Expression. In alternative embodiments, using long-term expression conferred by AAV-mediated gene transfer, transgene expression is regulated to turn off expression if unexpected untoward effects are seen. Regulated expression would also enable intermittent rather than constant delivery. In alternative embodiments, the system can be configured so that the activator either turns off or turns on transgene expression. In instances where nearly constant transgene expression is required, an "Off" system is desirable (e.g., one takes the oral activator only when transgene expression is not desired, for example in the event of adverse effects). In alternative embodiments, in instances where intermittent transgene expression is required, an "On" system is desirable (e.g., one takes the oral activator only for those times that transgene expression is desired).

TABLE 2

Tetracycline vs Rapamycin Regulation

| Feature | Tetracycline | Rapamycin Regulation |
|---|---|---|
| Activator | Doxycycline | AP22594 |
| Basal Expression ("leak") | Very low/none | None |

TABLE 2-continued

Tetracycline vs Rapamycin Regulation

| Feature | Tetracycline | Rapamycin Regulation |
|---|---|---|
| Linear Dose-Response | Yes | Yes |
| Activator Side-effects | Low (avoid in pregnancy) | Immuno-suppressant |
| Bacterial/Viral Proteins | Yes | No |
| Used in Clinical Trials | Not yet | Not yet |

TG, transgene; AP22594, oral rapamycin analog, 100-fold less immune suppression vs rapamycin[14]

These alternative embodiments enable tight control, and, when tailored for the specific disease treated, provide a means to take the least amount of activator. In alternative embodiments, regulated expression systems are used, e.g., ecdysone, tamoxifen, tetracycline, rapamycin[9-12]; the large size of the ecdysone system may require a two-vector strategy that would be difficult to develop for clinical gene transfer because of regulatory constraints. The tamoxifen system, while not as cumbersome, requires a less tolerated activator than the tetracycline system (tamoxifen vs doxycycline). In alternative embodiments, only two of the available options (tetracycline and rapamycin regulation) may be suitable, and these are the only systems that have been tested in large animal models.[3, 4] Both of these systems possess analogous features (Table 2, above): the gene of interest is controlled by an engineered transcription factor inducible by an activating drug (tetracycline or a rapamycin analog).

Tetracycline-Regulated Expression. In alternative embodiments the invention uses tetracycline-regulated expression in the setting of gene transfer:

a) Basal expression of transgene ("leak"). Newer rtTA variants, such as the one we propose and have used in recent studies (rtTA2$^S$-M2), provide robust tetracycline-dependent expression with no basal activity,[13] unlike previous rtTA constructs.

b) Chronic use of tetracycline vis-à-vis patient tolerability and off target effects.

The tet-regulation system has been extensively studied;[11] in vitro studies show that doxycycline-stimulated transgene expression begins at 0.001 ng/ml and reaches a maximum at 0.1 µg/ml, a 10-fold reduction in EC50 vs the first generation system.[13] In humans, a single oral dose of 200 mg doxycycline provides mean plasma and tissue concentrations of 1.5 µg/ml at 24 h,[14] 15-fold higher than required for maximal expression. A single daily dose of doxycycline of 10-20 mg may suffice for complete activation of transgene expression in human subjects.[15] Doses of 200 mg/d are well-tolerated by patients using oral doxycycline chronically for acne and chronic infections.[14,16]

ORACEA® (doxycycline 40 mg orally once daily) is approved by the FDA for continuous use to treat rosacea.[16] This dose, 80% lower than the 200 mg dose required to treat infection, provides anti-inflammatory effects that treat rosacea, but does not have anti-microbial effects, and does not lead to the development of antibiotic-resistant organisms (11 years of clinical data). Each capsule contains 40 mg of anhydrous doxycycline as 30 mg of immediate-release and 10 mg of delayed-release beads. Subjects with allergies to tetracycline, increased photosensitivity, pregnant or lactating women, or children less than 9 years old (discoloration of teeth, possible reduced long bone growth) should not use doxycycline. In 5 years of clinical use, the most common side effect was mild gastrointestinal complaints.[16]

Tetracyclines may attenuate matrix metalloproteinase expression and activity, and have an impact on left ventricular (LV) remodeling when administered in the first few days after myocardial infarction (MI).[17] However, in the proposed preclinical studies, doxycycline is administered 5 weeks after MI, when LV chamber dilation and scar formation are stable and equal among groups. We have previously documented that doxycycline does not influence LV remodeling, TIMP, or MMP expression in the proposed murine MI-induced CHF model.[18] In the clinical setting, tetracycline will not be used in the acute phase of MI.

c) Immune responses to the components of the rtTA system. Immune responses to the tet-regulator were not identified in a long-term study that used AAV4.tet and AAV5.tet gene transfer (intra-retinal) in non-human primates,[3, 15] where they saw sustained tetracycline-dependent transgene expression for the 2.5 year duration of the study. We do not see inflammation in mouse hearts expressing high levels of rtTA,[18, 19] or in mice and rats after AAV5-mediated regulated expression of IGFI using the rtTA2$^S$-M2 regulation element.[5] It appears that intramuscular delivery of AAV.tet in nonhuman primates, unlike intra-retinal or vascular delivery, does lead to attenuation of regulated expression, owing to immune responses to the bacterial and virus component of the transactivator fusion protein.[20] Immune response to the tet-regulator can be and simultaneously, the rapamycin-regulation system, which does not possess bacterial or virus proteins, and is not associated with provocation of the immune response, can be determined.[7] See Table 2 for strengths and limitations of tet- and rapamycin regulation.

Rapamycin-Regulated Expression. In alternative embodiments, a macrolide sirolimus (rapamycin), a product of the bacterium Streptomyces hygroscopicus, is used: it was initially developed as an anti-fungal agent, but was found to have anti-proliferative and immunosuppressant effects. Currently it is used clinically: a) to prevent rejection in organ transplantation (2 mg P.O. (per os, orally), once daily, which provides mean serum levels of 12±6 ng/ml); and b) in drug-eluting stents to reduce restenosis after angioplasty, owing to its antiproliferative effects. Rapamycin increases life span in mice, appears to forestall deleterious effects of aging,[21] and is used as an adjuvant in the treatment of glioblastoma multiforme.[22] Rapamycin binds cytosolic FK-binding protein 12 (FKBP12) and inhibits the mammalian target of rapamycin (mTOR) signaling pathway. A serine/threonine protein kinase, mTOR influences cell growth and proliferation, and promotes cell survival. Rapamycin's usefulness vis-à-vis gene therapy lies in its dimerization properties, a feature that is exploited in the rapamycin-regulated expression system. In this system, the DNA-binding and activation domains of an engineered transcription factor are expressed separately as fusion proteins, which are cross linked, and thereby activated, by the addition of a bivalent "dimerizing" drug, in this case rapamycin or a rapamycin analog.[12] Expression is dose-dependent, reversible, and is triggered by nanomolar concentrations of activator.[12] The rapamycin system contains no virus or bacterial proteins, and is therefore unlikely to incite an immune response. In macaques, intramuscular injection of AAV1 encoding erythropoietin provided up to 6 year (yr) Rap-regulated expression (26 separate induction cycles) with no decline in levels of erythropoietin, and no immune response to the regulation elements.[4] Immunosuppression is a potential disadvantage to rapamycin. However, this problem can be circumvented by using an oral rapamycin analog (AP22594), which activates transgene expression as effectively as rapamycin, exhibits minimal immune suppression, and does not inhibit mTOR.[4] Furthermore, as an activator, weekly rather than daily doses are effective, further reducing off-target effects. The dose-response relationship of orally administered AP22594, and its maximal dose-intervals, starting with oral doses used effectively in macaques (0.45 mg, once weekly), can be determined in pigs.[4]

Insulin-like Growth Factor I (IGFI)

Selection of IGFI. Growth hormone (GH) exerts many of its effects through activation of IGFI. IGFI exerts many of its effects through Akt. Because of the convergence of signaling from GH through IGFI to Akt, the selection of IGFI over GH or Akt must be defended. Increased GH expression would be predicted to increase serum glucose and blood pressure—deleterious effects that are avoided by selecting IGFI. Increased expression of Akt would be expected to reduce apoptosis, but have other potentially favorable effects not provided by Akt, such as increased angiogenesis. We therefore selected IGFI gene transfer for our initial preclinical CHF studies, and recently shown that IGFI gene transfer improves function of the failing rat heart[5] (see FIGS. 1-8 and Tables 4 & 5).

IGFI Signaling. IGFs, initially known as somatomedins, are a family of peptides that mediate many of the anabolic and mitogenic activities of GH. Two somatomedins with structural and metabolic similarities to insulin were isolated from human plasma in 1978 and named IGFI and IGFII. IGFI (somatomedin C) subsequently was shown to be the IGF regulated by circulating GH. IGFI has 70 amino acids in a single chain with 3 disulfide bridges and a molecular weight of 7.6 kD. Initially thought to be generated only by the liver, it has been shown to be produced by many tissues, including intestine, brain, kidney, lung and heart. Liver-specific deletion of the IGFI gene in rats does not alter normal growth and development,[23] indicating that IGFI, expressed widely in other tissues including heart, regulates growth and development through local tissue release in a paracrine manner.

IGFI belongs to a family of proteins including ligands (IGFI, IGFII, insulin), six known binding proteins (IGFBP 1-6), and cell surface receptors including IGFI and insulin receptors.[24] IGFI is translated as a pre-pro peptide which includes an amino terminal signal peptide, A, B, C and D domains and a variable carboxyl terminal E peptide. There are three known isoforms of pro-IGFI in humans (pro-IGFIa, pro-IGFIb and pro-IGFIc) that differ only in the amino acid composition of the variable E peptide. IGF binding proteins (IGFBP) act as carrier proteins and prolong the half-life of IGF by inhibiting degradation.[24] Almost all (98%) of IGFI circulates bound predominantly (80%) to IGFBP-3.[24]

IGFI and IGFII display high affinity binding to the IGFI receptor in all tissues except liver. The IGF receptor shares 60% homology with the insulin receptor and contains a tyrosine kinase domain. Receptor binding of IGFI results in autophosphorylation of tyrosine residues. This activates the receptor, producing phosphorylation of substrates including the insulin receptor substrate, which activates multiple signaling cascades including the PI3 kinase/Akt and mitogen activated protein kinase (MAPK) pathways, and others, many of which have beneficial cardiovascular effects (see below Sections and Table 3).

Effects of Increased IGFI. Increased serum IGFI lowers serum insulin levels, increases insulin sensitivity and improves lipid profiles.[24] However, infusion of IGFI protein can cause hypotension and hypoglycemia.[25] GH, which opposes insulin activity, increases serum glucose levels. The ability of IGFI to increase glucose uptake in the heart may play a role in post ischemic recovery of LV function after IGFI administration. IGFI increases muscle blood flow and has vasodilator activity, through receptor dependent and independent effects and nitric oxide production.[26] The combined metabolic and vasodilator effects of high-dose intravenous IGFI infusion in humans may cause lightheadedness and flushing—lower doses increase cardiac performance, do not affect blood pressure or serum glucose, and are unassociated with symptoms.[25,27]

IGFI receptor activation is responsible for numerous cellular responses including regulation of gene expression, stimulation of myogenesis, cell cycle progression, immune modulation, and steroidogenesis. In the heart, IGFI and the IGFI receptor/PI3K/Akt signaling pathway have beneficial effects on cardiac myocyte function, growth and survival. Moreover, IGF exhibits angiogenic effects,[28] increases cardiac contractile function in normal[25, 29, 30] and failing hearts,[27, 29, 30-33] and inhibits apoptosis.[34, 35, 38] These features make IGFI attractive for CHF therapy (Table 3).

IGFI Protein in Treatment of Heart Disease (Table 3)

TABLE 3

IGFI Beneficial Cardiovascular Effects

| Feature | Mechanism | Species | Ref |
|---|---|---|---|
| ↓ SVR | Vasodilation via NO | R, P, H | 25,26,32,39* |
| ↑ LV dP/dt, EF or CO | Inotrope; vasodilation | R, D, H | 25,29,30,36 |
| ↑ LV Function in CHF | Inotrope, ↑ $Ca^{2+}$ handling | R, D, P | 27,29-33,39* |
| ↑ Cardiac Protection | ↓ Apoptosis via Akt | M, R | 34,35,38 |
| ↑ LV Mass | CM prolif; ↓ Apoptosis via Akt | M. R | 31,36,45,46 |
| ↑ Blood flow | Angiogenesis | R | 28 |

SVR, systemic vascular resistance;
CO, cardiac output;
EF ejection fraction;
LV, left ventricular;
prolif, proliferation;
M mouse;
R, rat;
D, dog;
P, pig;
H, human;
39* used GH, which elevated IGFI 2-fold Preclinical Studies. The effects of administering recombinant human IGFI or GH protein in animal models of heart diseases have been studied. IGFI is a positive inotrope in isolated rat hearts and ferret papillary muscle; GH has no inotropic effect in the same tissues.[29] Similar inotropic effects of IGFI were found in isolated papillary muscles from dogs with pacing induced heart failure.[30] IGFI administered to normal rats for four weeks increased cardiac function and resulted in concentric LV hypertrophy.[31] IGFI and GH administered together for two weeks was associated with increased LV dP/dt and LV hypertrophy in normal rats.[36] Administration of IGFI prior to myocardial ischemia and reperfusion in rats decreased creatine kinase release and reduced apoptosis.[34] Combined IGFI and GH[32] or IGFI alone[33] administered four weeks after MI increased LV function in rats. GH given to rats for four weeks after MI increased LV systolic function,[37] reduced cardiac fibrosis, cardiac myocyte apoptosis, and increased survival.[38] In the pacing model of CHF in pigs, GH increased serum IGFI, increased LV function and reduced LV wall stress.[39]

Clinical Studies. Clinical use of GH or IGFI protein has received considerable attention, although there is a paucity of large placebo-controlled studies. The acute hemodynamic effects of IGFI infusion were studied in a blinded placebo-controlled crossover study of CHF patients (n=8). Four-hour infusions of IGFI increased cardiac output, decreased vascular resistance, and reduced right atrial and wedge pressures.[27] Chronic administration of IGFI protein has not been evaluated in patients with CHF. Use of GH protein in patients with CHF has produced equivocal results. Two small uncontrolled and unblinded studies in a total of 14 patients with CHF reported that three months of GH protein therapy increased serum IGFI, LV function and clinical status.[40, 41] Randomized placebo-controlled trials of GH (protein) given for up to 3 months in patients with CHF did not alter LV function or clinical status.[42, 43] The most recent literature review of GH protein therapy concludes that evidence for efficacy in ischemic and idiopathic clinical CHF is lacking, perhaps due to the kinetics of peptide administration.[44] Thus, in alternative embodiments, the gene transfer methods of this invention, by providing sustained IGFI expression, can be superior to IGFI protein therapy.

Increased Expression of Cardiac IGFI or GH. Cardiac-directed expression of human IGFI in rats, with its attendant increase in cardiac myocyte IGFI production, nearly doubles serum IGFI levels. These rats have increased heart weights with cardiac myocyte hyperplasia, but no increase in cardiac myocyte volume.[35, 45] After MI, reduced cardiac myocyte apoptosis, and increased phosphorylation of Akt were found.[35] Cardiac-directed expression of IGFI attenuates age-related cell senescence with reductions in telomerase activity, telomere shortening and DNA damage. These rats show increased Akt activation, and increased LV function at 22 months of age vs age-matched transgene negative littermates.[46] Co-expression of cardiac IGFI in a cardiomyopathic background (crossbreeding paradigm) appears to prevent cardiac apoptosis, LV remodeling and LV dysfunction.[47] However, since CHF was never present, this strategy is not equivalent to treating already existing CHF, an approach that is a central theme in the current proposal.

To determine if GH gene transfer would influence LV remodeling after MI, rat cardiac muscle was directly injected with adenovirus encoding GH (Ad.GH) at the time of coronary occlusion.[48] Injections were made in the border zone between jeopardized and viable myocardium. Six weeks after MI and gene transfer, favorable effects were seen on LV end-diastolic dimension, LV dP/dt and wall thickness in the infarct region. The same scientists subsequently showed that Ad.GH injected into the infarct border zone of rats three weeks after coronary artery occlusion increased LV dP/dt and attenuated LV dilation and wall thinning three weeks after injection.[49] GH gene transfer during or 3 w after MI appeared to have beneficial effects on LV remodeling.

When adenovirus encoding IGFI (Ad.IGFI) was injected into the jeopardized perfusion bed just before coronary occlusion in rats, the extent of infarction was reduced 50%, an effect thought primarily to be the result of reduced apoptosis.[50] This study did not address the effects of IGFI gene transfer on LV remodeling after MI. Adenovirus mediated gene transfer of IGFI has been shown to reduce hypoxia-induced myocyte apoptosis in vitro, and, in a rat ischemia reperfusion model, prior injection of adenovirus encoding IGFI reduced infarct size approximately 50% (p<0.003), although the transgene was expressed in only about 15% of the ischemic region, consistent with a regional paracrine effect. The effect of expressing IGFI in the globally failing heart has not been explored.

Potential IGFI Adverse Effects

Survival. Disruption of the GH/IGFI system appears to increase, not decrease longevity in rats with normal cardiac function.[51] However, we propose to increase IGFI expression in the setting of severe CHF, which portends markedly increased short-term mortality. No data suggest that IGF inhibition increases longevity in CHF. To the contrary, increased serum IGFI in humans reduces the incidence of CHF and mortality.[52, 53] Epidemiological studies have shown that people with low serum IGFI are at increased risk of developing ischemic heart disease. In the Framingham study, individuals above the median value for serum IGFI had a 50% reduced incidence of CHF compared to those below the median.[52, 53] A recent report shows that angiotensin converting enzyme inhibitors (ACEI), which prolong life in CHF, increases IGFI signaling.[54] Our data show that IGFI gene transfer increases function of the failing rat heart, and we propose to determine whether there also is a survival benefit.

Cancer. Clinical epidemiological studies report a correlation between increases in serum IGFI levels (>2-fold elevations) and prostate and premenopausal breast cancer,[55] but there is no indication that this correlation is causal. It is noteworthy that the incidence of prostate cancer increases with age, while serum IGFI concentration decreases.[55] In cancer patients, increased serum IGFI may originate in the tumor. Indeed, increased expression of IGFI in prostate epithelium of rats elevates serum IGFI concentrations and can lead to prostate neoplasia.[56] Increased serum IGFI concentrations may also result from changes in nutritional status in cancer patients. One could speculate that IGFI may increase tumor growth through angiogenesis and reduced apoptosis. Cardiac-directed expression of IGFIb, with attendant sustained elevations in serum IGFI, is not associated with prostate or breast cancer and combined increases in serum IGFI and GH do not increase the incidence of prostate, breast or lung cancer in patients with acromegaly.[54] The role of IGFI in the genesis or progression of cancer is theoretical. It seems prudent that therapies that increase IGFI expression should limit serum concentrations of IGFI, and also provide a means to stop expression if desired. We propose to achieve these goals by using gene transfer of a regulated expression vector, which increases IGFI concentrations in the serum and thereby has beneficial cardiovascular effects.

Novelty of Studies. These studies are focused on the development of IGFI gene transfer for clinical CHF. IGFI (or GH) gene transfer has not been used in clinical CHF. No double-blinded placebo-controlled clinical trial of GH/IGFI protein in CHF has been successful, perhaps due to the relatively short biological half-life of GH/IGFI protein, a problem that would be overcome by gene transfer. Although GH and IGFI cardiac gene transfer have been used prior to coronary occlusion to reduce infarct size in animal studies, no previous study has examined IGFI gene transfer for CHF per se. In addition, the proposed paracrine approach using systemic delivery of a long term and regulated expression vector is new, and can be applied to other paracrine-based peptides to treat a variety of cardiovascular diseases.

Summary. Because of the limitations of preclinical and clinical studies vis-à-vis predictable benefits of peptide administration of IGFI in the treatment of severe CHF, and the theoretical promise of paracrine-based gene transfer of IGFI, we embarked on studies in our laboratory (see Preliminary Data), designed to circumvent impediments and shortcomings of continuous or chronic intermittent intravenous peptide infusion.

Other Beneficial Peptides. Although the use of IGFI is compelling, it should be emphasized that the paracrine gene therapy methods of the invention are also suited for any circulating peptide with beneficial cardiovascular effects. For example, urocortin-2 is a recently discovered vasoactive peptide in the corticotropin-releasing factor family that acts via corticotropin-releasing factor type 2 receptors, which are robustly expressed in the heart and vasculature. Infusions of urocortin-2 peptide have protean beneficial effects in animals and patients with heart failure.[57] BNP is another biologically effective peptide for the treatment of clinical CHF that could be delivered in a similar manner. Moreover, in pulmonary hypertension, prostacyclin analogs can be effective in treating pulmonary hypertension, but current agents (epoprostenol and trepostinil) require constant systemic injection, and the treatment itself is associated with high morbidity.[58] In alternative embodiments, methods of the invention provide a regulated expression vector encoding prostacyclin synthase as a paracrine-type gene therapy of pulmonary hypertension. Indeed, any current peptide therapeutic that requires prolonged or chronic intermittent intravenous infusion, would lend itself to this hormone-like gene transfer approach.

AAV & Immune Response in Clinical Studies. Long-term transgene expression after intramuscular or intravascular delivery of AAV vectors has been the rule rather than the exception in rodents. However, studies in patients have been bedeviled by limited expression due to immune responses to the transgene and, at times, the AAV vector per se.[6] Two conclusions emerge from these and other studies. 1) Intramuscular (as compared to intravascular) AAV delivery generally provokes increased immune response to the transgene and AAV capsid; and 2) success in rodents, due to their relative immune tolerance, does not always predict success in humans. Rodent and pig studies can be designed with humans in mind:

AAV serotypes (AAV8 and AAV9) can be selected that are least likely to be associated with pre-existing neutralizing antibodies in human subjects.[59] For example, AAV8 is associated with the lowest prevalence of anti-AAV neutralizing antibodies (19% vs 59% for AAV1 and 50% for AAV2). Moreover, among the minority of human subjects with AAV8/9 antibodies, 75-90% of those subjects possess low titers, making AAV8 and AAV9 the current optimal choices vis-à-vis anticipated immune response.[59] Human sera possesses almost no seropositivity to rhesus-derived AAV vectors, such as AAVrh.32.33,[60] providing an alternative vector if AAV8 and AAV9 prove unsuitable, although preclinical and clinical experience with AAVrh.32.33 is limited.

Intramuscular injection of AAV vectors can be avoided because they may incite immune responses in larger animals.[6]

Two species-specific IGFI proteins can be used: rat and pig. Both rat and porcine IGFI can be used. The use of species-specific IGFI will reduce immune responses to the transgene. Clinical trials can be performed with the optimal vector encoding human IGFI.

Intravenous delivery of AAV8 and AAV9 is appealing because of its simplicity, and because it is likely to achieve the highest serum levels of therapeutic transgene at the lowest possible AAV dose. Although seroprevalence to these AAV vectors is important in pigs and primates, including humans, it has not been an important factor in rodents. Preliminary sampling of pigs from our vendor show no evidence of AAV8 or AAV9 antibodies in 7 of the 9 pigs tested.

In alternative embodiments, expression of a transgene of the invention is limited to a single organ, e.g., if such a strategy provides therapeutic serum levels of that transgene. For example, an exemplary vector of the invention is AAV8 with a hepatocyte-specific promoter (TBG, human thyroid hormone-binding globulin).

Paracrine-Based Gene Transfer Using IGFI.

Although we selected IGFI for these proof-of-concept studies, in alternative embodiments, the invention comprises use of any of the candidate genes outlined herein, and any of these genes would be effective for the intended effect. For example, the invention provides methods and compositions that effectively deliver any paracrine polypeptide, e.g., a mammalian cardiotonic peptide, a Serelaxin, a Relaxin-2, a Urocortin-2, a Urocortin-1, a Urocortin-3, a Brain Natriuretic Peptide, a Prostacyclin Synthase, a Growth Hormone, an Insulin-like Growth Factor-1, or any combination thereof; or, a human Urocortin-2, a Urocortin-1, a Urocortin-3, a Brain Natriuretic Peptide, a Prostacyclin Synthase, a Growth Hormone, an Insulin-like Growth Factor-1, or any combination thereof.

We engineered an exemplary AAV5 vector encoding rat IGFI (type A) that is under control of a tetracycline response element (TRE): FIG. 1 illustrates an exemplary construct of the invention comprising AAV5 encoding IGF1; this exemplary AAV5 vector provides regulated expression of IGFI: ITR, inverted terminal repeat; TRE, tetracycline response element; IGFIAU1, Insulin-like Growth Factor-I; SVpA, polyA from SV40 viral genome (bidirectional); rtTA2$^S$M2, reverse tetracycline controlled transactivator; CMV, human cytomegalovirus early gene promoter. Total insert size, 2823 bp, fits into a scAAV5 vector (capacity 3.3 kb).

Figure 2A:
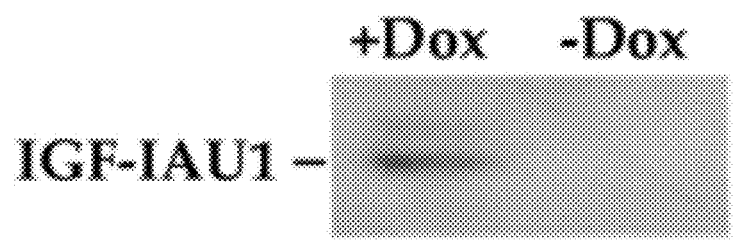
FIG. 2A-B illustrate data from studies where cultured neonatal rat cardiac myocytes were infected with the exemplary AAV5.IGFI.tet construct of the invention, and IGFI was induced, expressed, and then measured, as described in Example 2, below.
Figure 2B:
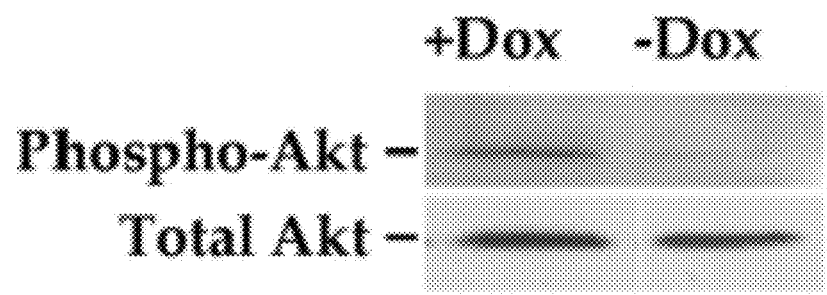

The coding sequence includes a signal peptide to ensure extracellular secretion of IGFI. We have used this vector (AAV5.IGFI.tet) in gene transfer experiments in cultured cardiac myocytes: FIG. 2A illustrates data from studies where cultured neonatal rat cardiac myocytes were infected with AAV5.IGFI.tet (10,000 gc/cell, 2 d); the gels illustrated show that IGFI expression was induced by doxycycline (+Dox) (2 µg/ml, 3 d), but did not occur in the absence of doxycycline (-Dox). IGFI was detected in media by anti-AU1 antibody by immunoblotting. FIG. 2B illustrates data where in the same experiments cardiac myocytes were lysed in Akt lysis buffer (10 min, 4° C.) and centrifuged (12,000× g, 10 min); total Akt and phospho-Akt were detected by anti-Akt and anti-phospho-T308-Akt antibodies. IGFI expression was associated with Akt activation. After infection, transgene expression was undetectable (no "leak") until activation with doxycycline (FIG. 2A).

Our vector (FIG. 1) contains a more recent rtTA variant (rtTA2$^S$-M2), which provides robust dox-dependent expression and low or absent basal activity, unlike previous rtTA constructs.[13]

Regulated IGFI Expression in Cultured Cardiac Myocytes

Cultured neonatal rat cardiac myocytes underwent gene transfer with AAV5.IGFI-tet ($10^4$ gc/cell, 2 days). As graphically illustrated in FIG. 3, subsequently, doxycyline (2 µg/ml) was added to media, and IGFI mRNA expression was quantified using real-time RT-PCR. Expression of IGFI mRNA was increased (versus vs unstimulated) by 1.5-fold within 30 min, and reached a peak of 14-fold elevation by 24 hrs. At 48 hrs, IGFI mRNA was somewhat less (10-fold), reflecting doxycycline degradation. To turn-off IGFI expression doxycycline was removed using four sequential PBS washes ("off-wash," see FIG. 3). IGFI mRNA rapidly decreased after doxycycline withdrawal.

Skeletal Muscle Delivery of AAV5.IGFI.tet Improves Function of the Failing Heart Skeletal Muscle Gene Transfer. We initially performed studies in murine heart failure after indirect intracoronary delivery of AAV5.IGFI.tet (FIG. 1), finding substantial improvements in function of the failing heart after cardiac-targeted delivery. However, proof-of-concept studies to demonstrate the efficacy of a paracrine-based transfer, would require skeletal muscle delivery of the vector. For these pivotal studies, we used intramuscular delivery of AAV5.IGFI.tet in the tibialis anterior muscle of rats.[5] AAV5 was selected because of its well-known high expression levels after IM injection in skeletal muscle. In all instances we have found IGFI expression in media (cell culture experiments), and long term IGFI expression in heart (murine CHF model) and in serum (rat model after IM injection, mouse after IV injection), and corresponding improvement in function of failing heart.[5]

Figures 4A, 4B, 4C:
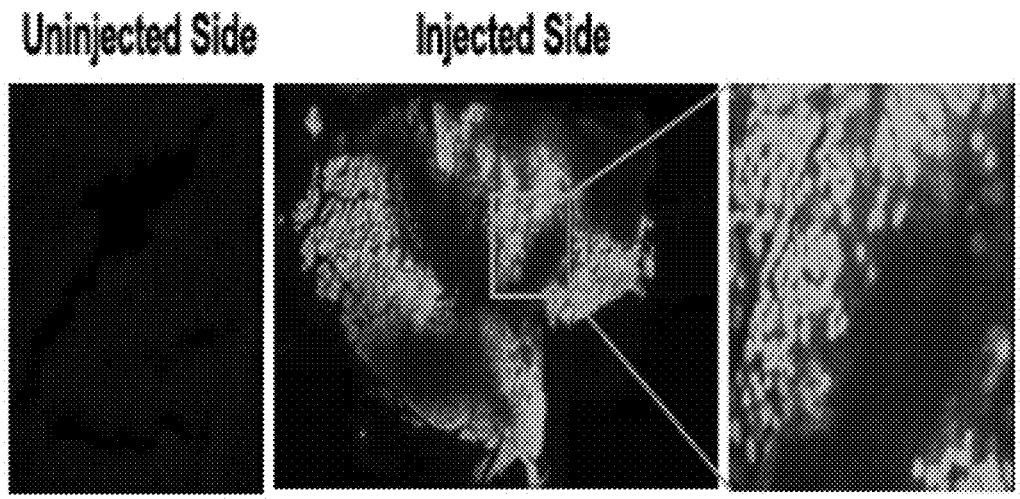
FIG. 4A-C illustrate photomicrographs showing EGFP expression in unilateral tibialis anterior muscle 3 weeks after AAV5.EGFP gene transfer in rats.

In the rat study, we first examined the feasibility of skeletal muscle injection of AAV5.EGFP to provide long-term transgene expression, as illustrated in FIG. 4A: illustrating photomicrographs showing EGFP expression in unilateral tibialis anterior muscle 3 weeks after AAV5.EGFP gene transfer in rats. Contralateral uninjected tibialis anterior muscle from the same animal shows no expression of EGFP. FIG. 4D is Table 4, which summarizes data from the echocardiography measuring the effects of Skeletal Muscle IGFI Expression in CHF; HR, heart rate; EDD, end-diastolic diameter; ESD, end-systolic diameter; EF, LV ejection fraction. Data denote mean±SE. Probability values from 2-way ANOVA, showing IGFI effect. Reference 5.

MI Model of CHF & Experimental Protocol

Figure 5:
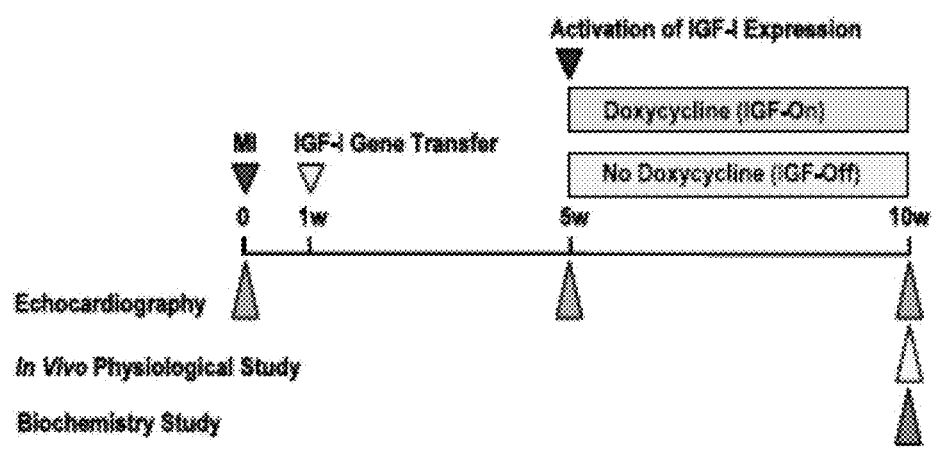
FIG. 5 illustrates the experimental protocol for gene transfer of the exemplary AAV5.IGFI.tet of the invention in skeletal muscle in CHF, as described in Example 2, below.

MI was induced in rats by proximal left coronary occlusion, resulting in large transmural infarction and severe impairment of LV function. One week after MI, rats with impaired LV function received $2\times10^{12}$ genome copies (gc) of AAV5.IGFI.tet in the anterior tibialis muscle. Four weeks later (5 w after MI), rats with LV ejection fraction (EF) <35% were randomly assigned to two groups: one group received doxycycline in drinking water to activate IGFI expression (IGF-On; n=10) and the other did not receive doxycycline (IGF-Off; n=9). Ten weeks after MI (5 w after activation of IGFI expression), LV size and function were assessed by echocardiography and hemodynamic studies; FIG. 5 illustrates the experimental protocol for AAV5.IGFI.tet skeletal muscle gene transfer in CHF.

Outcome. IGF-On rats showed increased LV ejection fraction (p=0.02) and reduced LV end-systolic dimension (p=0.03) (Table 4, see FIG. 4D). Furthermore, LV contractile function, assessed by the rate of pressure development (LV +dP/dt) during dobutamine infusion, was increased after initiation of IGFI expression (p=0.001) (Table 5, see FIG. 26). In addition, favorable changes in cardiac output (p=0.007) and stroke work (p=0.003) were observed (Table 5). Serum IGFI was increased 5 wk after transgene activation (IGF-Off: 164±24 ng/ml; IGF-On: 218±11 ng/ml; p=0.008; n=9 each group). These data indicate that skeletal muscle injection of AAV5.IGFI.tet enables tetracycline-activated expression, increases serum IGFI levels, and improves function of the failing heart.[5] In alternative embodiments, less immunogenic AAV vectors can be used, and they can be used intravenously rather than in an intramuscular injection to circumvent inciting immune responses, and test two regulated expression systems.

Cardiac Apoptosis and Fibrosis (FIG. 6)

Figure 6A:
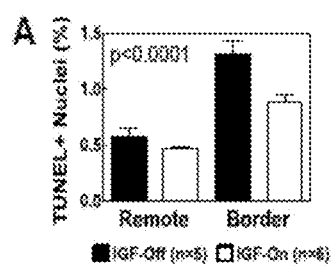
FIG. 6A-C illustrate the effects of AAV5.IGFI-tet gene transfer on cardiac apoptosis and fibrosis.
Figure 6B:
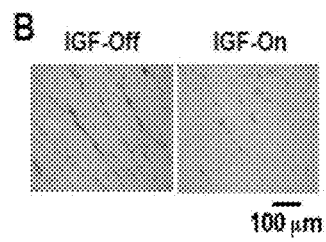
Figure 6C:
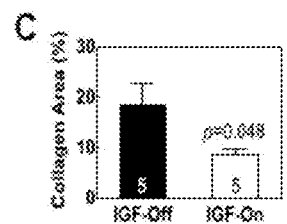

FIG. 6 illustrates the effects of AAV5.IGFI.tet gene transfer on cardiac apoptosis and fibrosis. FIG. 6A graphically illustrates data from TUNEL staining that indicated that activation of IGFI expression (IGF-On) was associated with reduced cardiac myocyte apoptosis (p<0.0001; 2-way ANOVA), which was reduced more in the border than remote region. FIG. 6B illustrates picrosirius red-stained sections of the uninfarcted intraventricular septum from IGF-Off and IGF-On rats that showed reduced cardiac fibrosis, and collagen fractional area was reduced (p=0.048); FIG. 6C graphically illustrates this data from the IGF-Off and IGF-On rats.

Intravenous vs Intramuscular Delivery of AAV5.IGFI.tet. In preliminary studies, we determined whether intravenous gene transfer could increase circulating IGFI levels. One week after intravenous delivery of AAV5.IGFI.tet ($5\times10^{10}$ gc per mouse, tail vein) mice were randomly assigned to one of two groups: one group received doxycycline in drinking water to activate IGFI expression (IGF-On) and the other did not receive doxycycline (IGF-Off). Since the majority of circulating IGFI is bound to IGFI binding proteins (IGFBPs) with high affinity and is biologically inactive, we measured free serum IGFI, the bioactive IGFI form, which was 2-fold higher in IGF-On than in IGF-Off mice 3 months after activation of IGFI expression (FIG. 7, next page). Using the intramuscular AAV5.IGFI.tet ($2\times10^{12}$ gc per rat) gene transfer strategy outlined in Section 2.2.1.2., we found a 1.3-fold increase of free serum IGFI in IGF-On group than IGF-Off group 5 weeks after activation of IGFI expression (FIG. 7). These data suggest that intravenous delivery of AAV5.IGFI.tet is more effective than intramuscular delivery vis-à-vis serum IGFI concentrations.

Moreover, an intravenous strategy is likely to circumvent provocation of immune response, which has been observed following intramuscular delivery of AAV.[6] These experiments provide pivotal feasibility data for our studies.

Intravenous Delivery: AAV5 vs AAV9.

We next determined the relative efficacy of intravenous delivery of AAV5 vs AAV9, using copy number and transgene expression in liver and heart as endpoints, as illustrated in FIG. 8. We used self-complementary (sc) AAV vectors, enabling earlier expression vs single-strand (ss) AAV vectors. Mice received intravenous scAAV5.CMV.EGFP or scAAV9.CMV.EGFP ($5\times10^{11}$ gc) and were killed 21 d later. PCR primers directed to common sequences in both vectors were used to compare AAV DNA copy number in liver and heart. In liver, AAV9 (vs AAV5) provided 3-fold increases in both AAV DNA copies and in EGFP expression; in heart, a 5-fold increase in AAV DNA copies and an 8-fold increase in EGFP expression were seen. These data show that, compared to intravenous AAV5, AAV9 can provide higher serum levels of transgene.

Methods

FIG. 10 illustrates exemplary vectors and vector designs of the invention: Using intravenous delivery of three vectors selected from preliminary studies and biological features, the relative merits of widely distributed and expressed AAV8 and AAV9 (FIG. 10A), and AAV8 with a liver-specific promoter (FIG. 10B) can be determined. The criterion for effectiveness can be serum levels of IGFI 6 weeks (w) after delivery. An optimal AAV vector is used to generate two regulated expression vectors (Tet and Rap), which can be compared following intravenous delivery in rats, as illustrated in FIG. 10C-F. The criterion for effectiveness can be serum levels of IGFI, this time examined 16 w after activation of transgene expression (20 w after delivery).

Figure 10A:
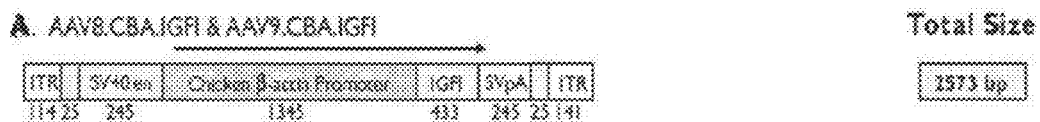
FIG. 10A-F illustrate exemplary vector constructs of the invention, as described in Example 2, below.
Figure 10B:
Figure 10C:
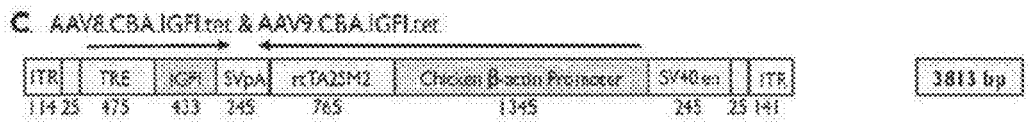
Figure 10D:
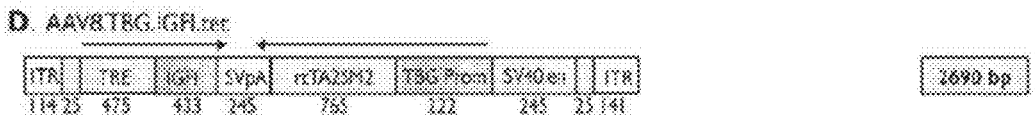
Figure 10E:
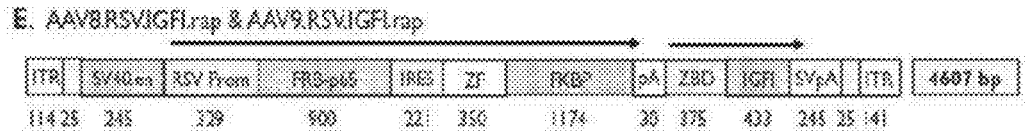
Figure 10F:
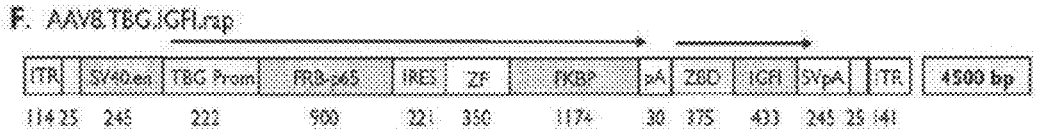

FIG. 10A & B. AAV vectors for the initial studies in rats to determine the best AAV serotype for subsequent studies. These vectors encode rat IGFI (unregulated), driven by CBA (AAV8 & AAV9) or TBG (AAV8). The best of these, based on serum IGFI levels and duration of expression, can be used to undergo subsequent studies to determine the optimal regulation system.

FIG. 10C-F. Candidate vectors for studies in rats to determine the optimal regulated expression system. Using the best AAV vector from the initial studies (above), 2 regulated expression vectors are generated and tested: one with Tetracycline-regulation, the other with Rapamycin-regulation. These vectors encode regulated expression of rat IGFI, driven by RSV (AAV8 & AAV9) or TBG (AAV8). The CBA promoter is too large for the Rapamycin-regulation vector, so RSV is used instead. The better of these two regulation systems is selected for generation of the optimal vector for the subsequent studies in normal pigs, encodes for regulated expression of porcine IGFI. ITR, inverted terminal repeat; TRE, tetracycline response element; IGFI, Insulin-like growth factor-I; SVpA, polyA from SV40 virus genome (bidirectional); rtTA2$^S$M2, reverse tetracycline controlled transactivator; SV40en, simian virus 40 enhancer; TBG Prom, thyroid hormone-binding globulin promoter; RSV Prom, Rous sarcoma virus promoter; FRB-p6, part of FRAP, a rapamycin interacting protein, combined with a subunit of transcription factor NF-κB (p65); IRE, internal transcription reentry site; ZF, zinc finger HD1 DNA binding domain; FKBP, FK506 binding protein; pA, minimal polyadenylation segment; ZBD, zinc finger HD DNA binding domain (8 copies).

We do not anticipate that immune responses to AAV will play an important role in rats, although such responses are important in dogs, pigs, humans and other primates. Immune responses should be carefully assessed. AAV biodistribution (e.g., using qPCR using primers amplifying common sequences in all vectors) and toxicity (e.g., using histological analysis) can be quantified.

Group Size. The primary criterion for success can be serum level of IGFI, which has a coefficient of variation of 20%. To detect a 30% difference in serum IGFI between groups, assuming an α error of 0.05 and a β error of 0.10, will require a group size of n=10.

Example 3

Delivery of AAV8 Encoding Urocortin-2 Increases Cardiac Function

This example demonstrates that in alternative embodiments of methods of this invention a paracrine transgene acts as a hormone and has cardiac effects after being released to the circulation from a distant site. This exemplary approach can circumvent the problem of attaining high yield cardiac gene transfer and enable patients to be treated by a systemic injection during an office visit. Furthermore, this exemplary approach can eliminate the need for intravenous (IV) delivery of therapeutic peptides and thereby circumvent repeated and prolonged hospital stays, high morbidity, and enormous economic costs. In alternative embodiments, the most suited vector to achieve these goals is the adeno-associated virus type 8 (AAV8), which provides long term and extensive expression after intravenous delivery in rodents, pigs, and primates.

In alternative embodiments of methods Urocortin-2, a recently discovered corticotropin releasing factor family vasoactive peptide, is used as a therapeutic transgene. Urocortin-2 can act via corticotropin-releasing factor type 2 receptors, which are robustly expressed in the heart and vasculature. Studies in animals and patients with congestive heart failure have shown favorable hemodynamic effects of urocortin-2 peptide infusions, including increased contractile function independent of loading, indicating direct cardiac effects. We established that intravenous delivery of AAV8 using the chicken β-actin promoter provides sustained high serum levels of UCn2 and increases function of the failing mouse heart.

To select the best specific embodiments to practice this aspect of the invention, studies in mice and pigs can be carried out, e.g.,: a) determine regulated transgene expression to enable fine-tuning of plasma transgene levels, and allow turning expression off and on as needed; and b) determine the safety, efficacy, and mechanism of action of urocortin-2 gene transfer, using this exemplary paracrine-based approach in an art-accepted animal model, a mouse model of CHF. Also, use of normal pigs can determine: a) the minimally effective vector dose required to increase serum UCn2; b) biodistribution of the vector and transgene; and c) toxicity.

Potential advantages of paracrine gene transfer methods of the invention over IV peptide infusion are shown in Table 1 (above). In alternative embodiments, practicing methods of the invention allows circumvention of infection and reduced repeated and prolonged hospital stays, thereby reducing costs. In alternative embodiments, systemic vector delivery is an advantage in paracrine gene transfer by providing the highest level of expression for any given AAV dose. The potential safety and efficacy of this approach was recently demonstrated in an early phase gene therapy clinical trial in patients with hemophilia B,[2] a study that has restored hope in gene therapy. In alternative embodiments, paracrine gene transfer methods of the invention can be suited for any circulating peptide with beneficial cardiovascular effects.

Figure 11:
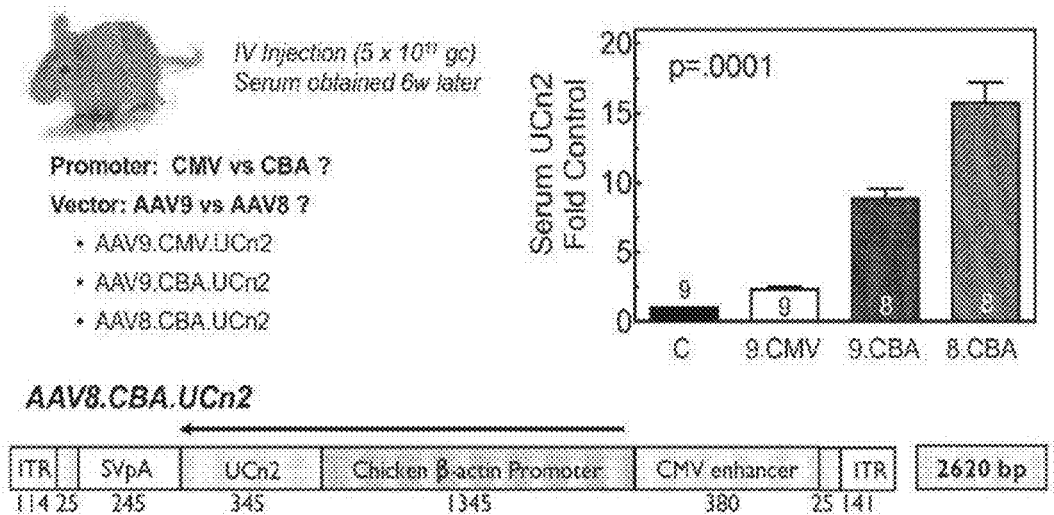
FIG. 11 graphically illustrates data showing that IV AAV8 is the optimal vector and delivery route to attain sustained increased levels of serum urocortin-2 (UCn-2) for a paracrine approach, as described in Example 3, below.

In alternative embodiments, AAV is used to enable longer transgene expression than adenovirus, and avoid insertional mutagenesis associated with retrovirus. Persistent transgene expression has been shown in large animals years after a single injection of AAV vectors.[6-10] We have confirmed this in mice[11] & rats. Although recent clinical trials have found that some AAV serotypes incite immune responses after IM injection,[12, 13] newer generation AAV vectors (AAV5, 6, 8 and 9) do not have similar problems in primates.[14] IV AAV delivery is superior to IM vis-à-vis serum transgene levels, and AAV9 and AAV8 are superior to AAV5[15] (and unpublished data). Moreover, pre-existing anti-AAV8 antibodies are not as prevalent in humans (19%) as are other AAV serotypes including AAV1 & AAV2 (50-59%).[16] Our data, graphically illustrated in FIG. 11, indicate that IV AAV8 is the optimal vector and delivery route to attain sustained increased levels of serum UCn2 for a paracrine approach. FIG. 11 illustrates data from: IV delivery of AAV9.CMV.UCn2 (9.CMV), AAV9.CBA.UCn2 (9.CBA) vs AAV8.CBA.UCn2 (8.CBA); where the data indicated that all vectors were associated with substantial increases in serum UCn2 6 w later. Numbers in bars denote sample size for each group; p value from ANOVA. ITR, inverted terminal repeat; SVpA, polyA from SV40 viral genome; UCn2, urocortin-2; CBA, chicken β-actin promoter; CMV enhancer, human cytomegalovirus enhancer.

Despite its robustness in striated muscle, the CMV promoter is susceptible to methylation and inactivation in liver,[17] and our data indicate that promoters less susceptible to methylation are superior. Indeed, although CMV provided a sustained 2-fold increase in UCn2 after IV vector delivery, use of the chicken β-actin (CBA) promoter resulted in 15.7-fold increase in serum UCn2, as illustrated in FIG. 11. The hepatocyte-specific thyroid hormone-binding globulin (TBG) promoter also can be used.

In alternative embodiments, the constructs and methods of the invention allow for regulated expression, e.g., turning off expression. Because of the potential for long-term expression conferred by AAV gene transfer, the ability to turn off expression is desirable in the event that untoward effects develop. Regulated expression also enables the flexibility of intermittent rather than constant transgene delivery. In alternative embodiments, the constructs and methods of the invention use regulated expression systems such as e.g.,: ecdysone, tamoxifen, tetracycline, rapamycin.[18-21] The size of the ecdysone system requires a two-vector strategy and tamoxifen presents issues with toxicity. Tetracycline and rapamycin regulation systems (Table 2) have been tested in large animal models[9, 10, 22-26]

TABLE 2

Tetracycline vs Rapamycin Regulation

| Feature | Tetracycline | Rapamycin Regulation |
|---|---|---|
| Activator | Doxycycline | AP22594 |
| Basal Expression ("leak") | Very low/none | None |
| Linear Dose-Response | Yes | Yes |
| Activator Side-effects | Low (avoid in pregnancy) | Immuno-suppressant |
| Bacterial/Viral Proteins | Yes | No |
| Used in Clinical Trials | Not yet | Not yet |

TG, transgene;
AP22594, oral rapamycin analog, 100-fold less immune suppression vs rapamycin[13]

In alternative embodiments, the constructs and methods of the invention use a tet-regulation system, which has been extensively studied.[27] Unlike previous rtTA constructs, rtTA variants of this invention (e.g., rtTA2$^S$-M2), provide robust tet-dependent expression with no basal activity (i.e. no "leak")[11, 26, 28, 29, 30] and 10-fold higher sensitivity to tetracycline (maximum transgene expression activation at 0.1 μg/ml).[30] A single daily dose of doxycycline of 10-20 mg may suffice for complete activation of transgene expression in human subjects.[26, 31] Doses of 200 mg/d are well tolerated by patients using oral doxycycline chronically for acne and chronic infections.[31, 32] Tetracyclines may attenuate matrix metalloproteinase (MMP) activity and affect LV remodeling when administered in the first few days after MI.[24] We have previously shown that doxycycline does not influence LV remodeling, TIMP, or MMP expression in the proposed murine MI-induced CHF model, where doxycycline is given 5 w after MI.[25] In clinical settings, tetracycline will not be used in the acute phase of MI.

Immune responses to components of the rtTA system, a potential problem, were not identified in a study of AAV4.tet and AAV5.tet gene transfer (intraretinal) in non-human primates,[9] where tetracycline-dependent transgene expression persisted for the 2.5 year duration of the study. We do not see inflammation in mouse hearts expressing high levels of rtTA,[25, 28, 29] or in mice after AAV5-mediated regulated expression of IGFI using the rtTA2$^S$-M2 regulation element.[11] It appears that IM delivery of AAV.tet in nonhuman primates, unlike intra-retinal or vascular delivery, does lead to attenuation of regulated expression, owing to immune responses to the bacterial and virus components of the transactivator fusion protein.[33] Immune response to the tet-regulator and the rapamycin-regulation system, which does not possess bacterial or virus proteins and is not associated with provocation of the immune response, can be simultaneously tested.[10] See Table 2 for strengths and limitations of tet- & rapamycin regulation.

In the rapamycin regulation system, transgene expression is triggered by nanomolar concentrations of rapamycin or a rapamycin analog, which is dose-dependent and reversible.[21] Rapamycin is used clinically to suppress immune response, forestalls deleterious effects of aging in mice[23] and inhibits glioblastoma multiforme[34] by blocking the mammalian target of rapamycin (mTOR) signaling pathway.[35] The oral rapamycin analog AP22594, which activates transgene expression as effectively as rapamycin, exhibits minimal immune suppression, and does not inhibit mTOR.[10, 35-37] Pigs can be used to determine the dose-response relationship of orally administered AP22594, and its required dosing intervals, starting with oral doses similar to those used effectively in macaques (0.45 mg/kg, once weekly).[10]

In alternative embodiments, the constructs and methods of the invention express in vivo Urocortin-2, including UCn1, UCn2 and UCn3 (38-40 amino acids (aa)), which belong to the corticotropin-releasing factor (CRF) family. These peptides can stimulate corticotropin-releasing factor receptors 1 and 2 (CRF1, CRF2). UCn1 binds to CRFR1 & CRFR2, but UCn2 & Ucn3 exclusively bind CRFR2,[38-41] which are expressed in cardiac myocytes, vasculature, gut, brain and skeletal muscle.[42, 43, 44] Although UCn1 was found in LPS-induced inflammation and was implicated in tissue permeability,[45, 46] UCn2's effects, which are diverse, have been associated with favorable biological effects, owing in part to its affinity for CRFR2. UCn2's effects are not entirely cAMP-dependent. For example, CRFR2 desensitization after UCn2 binding induces PI3K/Akt signaling via translocation of β-arrestin. In addition, increased ERK1/2 signaling occurs via disassociation of G protein β & γ subunits.[47, 48] These cAMP-independent events contribute to reduced cardiac myocyte apoptosis. Peptide infusions of UCn2 in preclinical and clinical CHF have consistently shown favorable effects on LV function, and reduced activation of the sympathoadrenal axis.[49-51]

As listed in Table 3, below, among many beneficial effects, UCn2 infusion using methods and compositions of the invention can increase contractile function independent of loading conditions, indicating direct cardiac effects.[52] The mechanisms for inotropic effects have not been defined. Recent studies suggest beneficial effects on Ca$^{2+}$ handling,[53] action potential duration,[54] ischemia-reperfusion injury,[55-57] and the renin-aldosterone system.[49] The safety and efficacy of UCn2 infusion has been confirmed in large animal models of CHF,[58, 59] and in normal human subjects & patients with CHF.[50, 51] A recent editorial promotes its use in Class 3 & 4 CHF.[60]

TABLE 3

Urocortin-2: Beneficial Cardiovascular Effects

| Feature | Mechanism | Species | Ref |
|---|---|---|---|
| ↓ SVR | Vasodilation via CRFR2 | M, S, H | 44,57-59 |

TABLE 3-continued

Urocortin-2: Beneficial Cardiovascular Effects

| Feature | Mechanism | Species | Ref |
|---|---|---|---|
| ↑ CO & EF | Inotrope; vasodilation | M, S, H | 44,57-59 |
| ↓ Cardiac Work | ↓ SVR and LAP | M, S, H | 44,57-59 |
| ↑ LV Diastolic Function | Lusotrope | M, R, S, H | 44,52,56 |
| ↑ Diuresis | ↑ RBF & Na excretion; ↓ RAS | S, H | 49,57-59 |
| ↑ LV function in CHF | All of the above are reported | M, R, S, H | 44,49,56,57,59 |
| ↓ LV IR Injury & apoptosis | Unknown | M, R | 53-55 |

SVR, systemic vascular resistance;
CRFR2, corticotropin-releasing factor receptor-2;
CO, cardiac output;
EF, left ventricular ejection fraction;
LV, left ventricular;
LAP, left atrial pressure;
RBF, renal blood flow,
RAS, renin-angiotensin system;
CM, cardiac myocyte;
IR, ischemia-reperfusion;
M, mouse;
R, rat;
S, sheep;
H, human Since plasma half-life of UCn2 is 15 min,[51] chronic infusion is required. In contrast, in alternative embodiments, paracrine-based UCn2 gene transfer of the invention can circumvent impediments associated with chronic peptide infusions, as noted in Table 1, above. By expressing only species-specific UCn2 in the two species proposed, immune responses to the transgene will be abrogated.

Paracrine-based Gene Transfer Proof of Concept. We proved that paracrine gene transfer via IM injection of AAV5 encoding Insulin-like Growth Factor-I (AAV5.IGFI) improves function of the failing rat.[11] We now also have shown that IV delivery of AAV8 encoding UCn2 not only provides sustained high levels of serum UCn2 (>15-fold increase), but increases function of normal and failing hearts.

Selection of AAV Vector and Promoter. It was clear from previous published studies that IV AAV8 or AAV9 would provide higher levels of transgene expression than other AAV serotypes, and CMV or CBA promoters, which generally are the most robust, would be optimal. Therefore we engineered an AAV8 & two AAV9 vectors encoding murine UCn2 driven by CMV or CBA to determine which vector would most effectively increase serum UCn2, as illustrated in FIG. 11. A commercially available UCn2-specific ELISA was used. AAV9.CMV raised serum UCn2 2.3-fold, which, while lower than the other 2 vectors, may be sufficient for a therapeutic response. However, AAV8.CBA was associated with a 15.7-fold rise in serum UCn2 (AAV8.CBA.UCn2: 109 ±7 ng/ml, n=9; Control: 7±1 ng/ml). Such a high level of serum UCn2 would enable reducing the AAV8 dose. The superiority of AAV8.CBA and AAV9.CBA over AAV9.CMV may reflect either CBA's relative robustness or CMV's susceptibility to methylation and inactivation in liver.[17] We therefore selected AAV8.CBA for additional studies.

AAV8.CBA.UCn2 Distribution & Expression After Intravenous Delivery. In alternative embodiments, the constructs and methods of the invention express in vivo by a paracrine-based gene transfer strategy UCn2, and can be used to increase serum levels of UCn2. Alternative embodiments do not require that UCn2 expression be present in the heart per se, because it is the effects of circulating UCn2 and its effects on the heart and vasculature that will provide the therapeutic effects of the transgene, effects that do not require UCn2 expression in cardiac myocytes themselves.

Figure 12A:
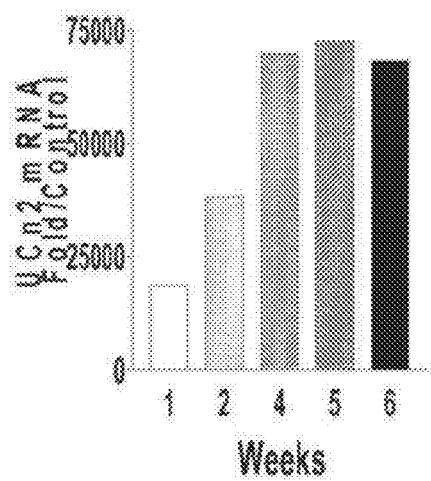
FIG. 12A-B.
Figure 12B:
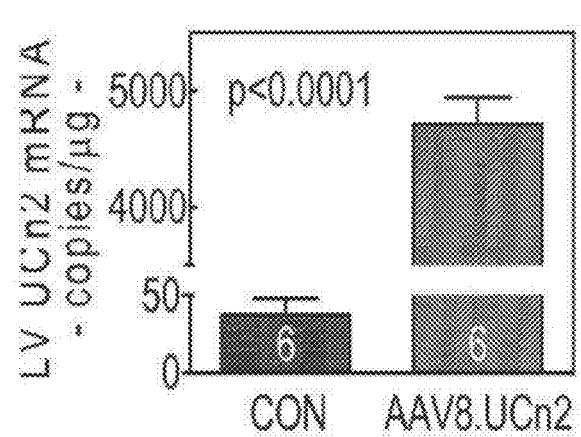

Liver Expression of UCn2. The 15.7-fold increase in serum UCn2 documented 6 w after IV delivery of AAV8.CBA.UCn2 ($5\times10^{11}$ gc; see FIG. 11) was associated with a time-dependent increase in UCn2 mRNA expression in liver, as illustrated in FIG. 12, that plateaued 4-6 weeks after delivery, which correlated well with the steady rise in serum UCn2. FIG. 12A graphically illustrates a time course of UCn2 mRNA expression in liver after AAV8.CBA.UCn2 ($5\times10^{11}$ gc, IV). Liver UCn2 expression (each bar is mean value from 2 mice) reached a plateau 4-6 weeks after delivery, which correlated with the plateau seen with serum UCn2 (data not shown). FIG. 12B graphically illustrates data showing UCn2 mRNA expression in LV 6 weeks (w) after AAV8.CBA.UCn2 ($5\times10^{11}$ gc, IV). Similar high levels of UCn2 mRNA were seen in skeletal muscle samples (data not shown).

Cardiac Expression of UCn2. Although cardiac expression of UCn2 is not required for the beneficial effects of the paracrine-based gene therapies of the invention, we documented substantial increases in UCn2 mRNA expression in LV samples 6 w after IV delivery of AAV8.CBA.UCn2, see FIG. 12B. In alternative embodiments, a construct of the invention, including e.g., AAV8, including AAV8 DNA presence and UCn2 mRNA, can be delivered to and/or expressed in any organ or other organs, including skeletal muscle, lung, brain, kidney, spleen, small intestine, bone marrow.

Figure 3:
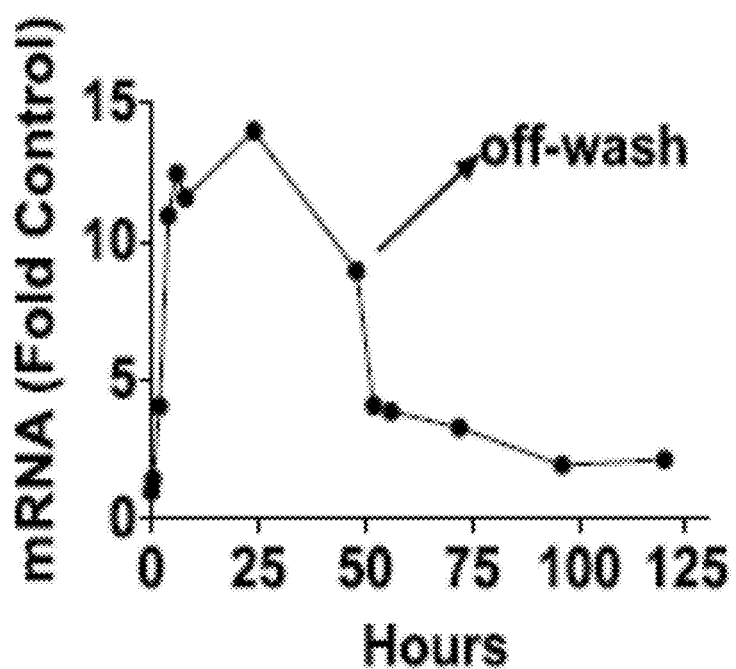
FIG. 3 graphically illustrates regulated expression of IGFI mRNA expression in cultured neonatal rat cardiac myocytes after gene transfer with the exemplary AAV5.IGFI-tet adding, and them removing, doxicillin, as described in Example 2, below.
Figure 13A:
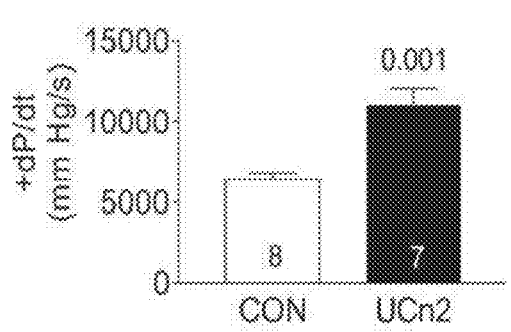
FIG. 13A-B graphically illustrates data from a study to determine if UCn2 gene transfer increased LV function by delivery of the exemplary AAV8.UCn2 construct of the invention by intravenous (IV) delivery in normal mice.
Figure 13B:
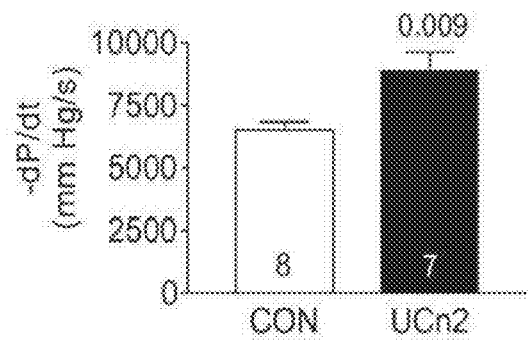

UCn2 Gene Transfer in Normal Mice. To determine if UCn2 gene transfer increased LV function, we delivered AAV8.UCn2 ($5\times10^{11}$ gc) or saline (control) by intravenous (IV) delivery in normal mice. Five weeks after UCn2 gene transfer, mice underwent an invasive procedure in which Millar catheters (1.4 F) were placed in the LV chamber to measure pressure development. Data acquisition and analyses were blinded to group identity. UCn2 gene transfer increased LV contractile function (LV +dP/dt) (FIG. 13A, left); −dP/dt also was reduced, indicating enhanced LV relaxation (FIG. 13B, right panel). No adverse effects on LV mass, histology, or LV structure or function were detected. FIG. 3 graphically illustrates: LV function in normal mice 6 weeks after IV delivery of AAV8.CBA.UCn2 (vs saline-injected control mice. FIG. 3A: LV +dp/dt; FIG. 3B. LV −dP/dt. Values represent mean±SE. Number in bars denotes group size. UCn2 gene transfer increased both contractile function and cardiac relaxation.

Figure 14A:
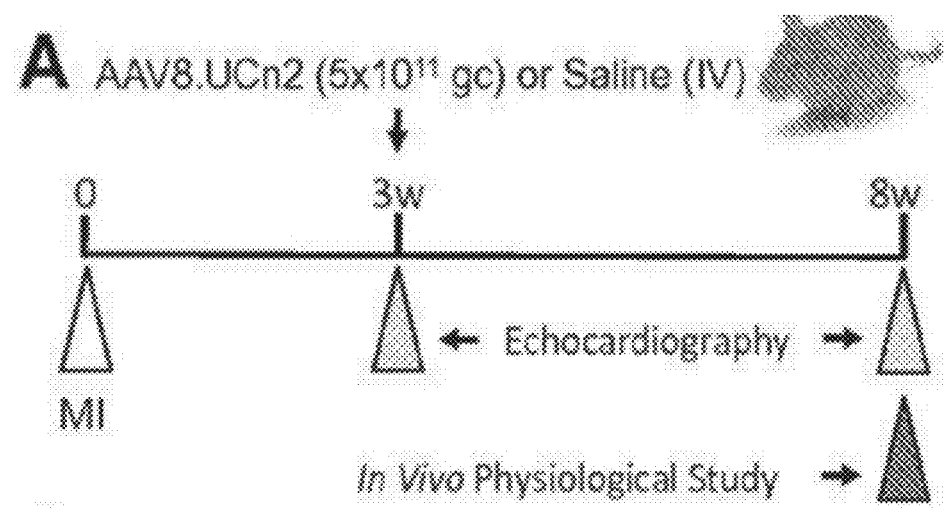
FIG. 14A-C illustrates data showing the effects of UCn2 transfer on the failing heart.
Figure 14B:
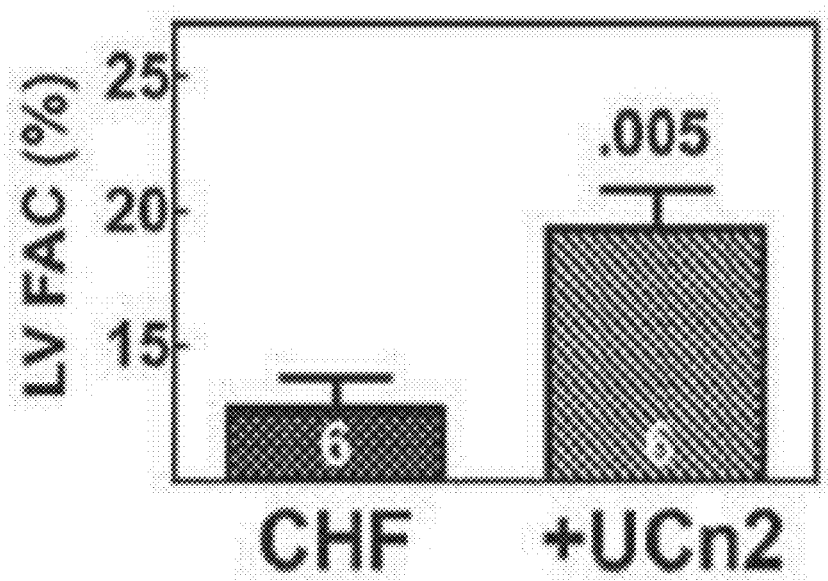
Figure 14C:
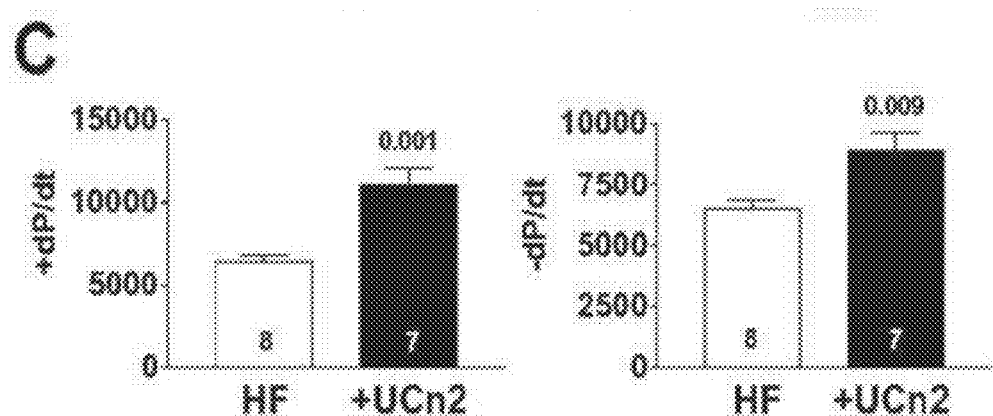

UCn2 Gene Transfer in Mice with CHF. We used proximal left coronary occlusion to induce severe CHF in mice, a model that we have used extensively and that mimics aspects of clinical ischemia-based CHF.[25] As shown in the protocol (FIG. 12A), 3 w after coronary occlusion, we performed echocardiography to confirm severe LV dysfunction and chamber dilation. We then randomly assigned enrollees to receive IV delivery of AAV8.CBA.UCn2 ($5\times10^{11}$ gc per mouse) or an equivalent volume of saline. Five weeks after randomization, mice underwent repeat echocardiography and measurement of LV pressure development and decay and their first derivative, LV +dP/dt. Data acquisition and analyses were blinded to group identity. Despite marked LV dysfunction that was present at the time of UCn2 gene transfer, LV fractional area change (FAC %), an ejection fraction surrogate, was increased (FIG. 14B). UCn2 gene transfer also increased LV systolic (LV +dP/dt) and diastolic (LV −dP/dt) function (FIG. 14C). Peak LV +dP/dt was increased to a value that approached normal, confirming that the proposed strategy merits development as a novel therapy for CHF. FIGS. 14B and 14C illustrate data showing the effects of UCn2 transfer on the failing heart: FIG. 14A: 3 w after MI and development of CHF, mice received IV AAV8.UCn2 or saline; 5 w after gene transfer (8 w after MI), LV function was assessed (blinded studies); FIG. 14B. UCn2 gene transfer increased LV fractional area change (%FAC); FIG. 14C. UCn2 gene transfer increased LV peak +dP/dt and peak −dP/dt, indicating marked benefits in systolic & diastolic LV function of the failing heart.

UCn2 Gene Transfer: Effects on Cardiac $Ca^{2+}$ Handling

C2.5.1.UCn2 Gene Transfer Alters Expression of SERCA2a. AAV8.CBA.UCn2 gene transfer ($5 \times 10^{11}$ gc, IV) was associated with increased expression of SERCA2a mRNA and protein in LV samples obtained from mice 4 w after gene transfer (FIG. 15). These changes would be anticipated to promote $Ca^{2+}$ availability to the myofilament, and thereby to increase both systolic and diastolic function, as we have observed in normal and failing hearts following UCn2 gene transfer (FIGS. 13 and 14), providing a plausible mechanism by which UCn2 gene transfer increases LV function. Similar effects of UCn2 peptide have been described in isolated cardiac myocytes.[53]

Figure 15A:
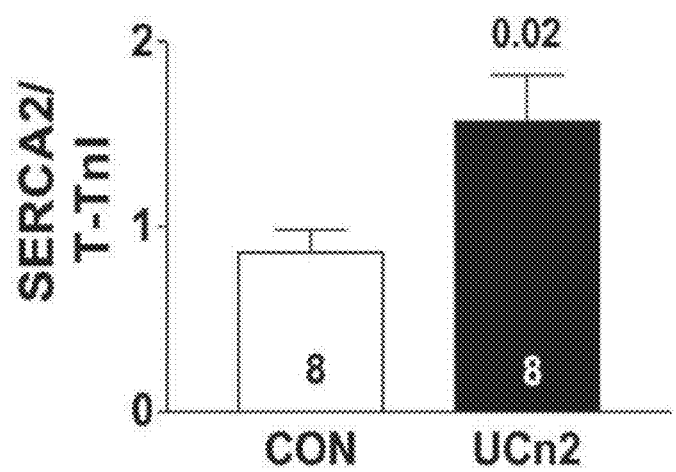
FIG. 15A-B illustrate data, FIG. 15A by graph, FIG. 15B by immunoblot, where normal mice received IV delivery of the exemplary AAV8.CBA.UCn2; and four weeks later, LV samples from the UCn2 gene transfer group showed a 2-fold increase in SERCA2a protein expression, as described in Example 3, below.
Figure 15B:
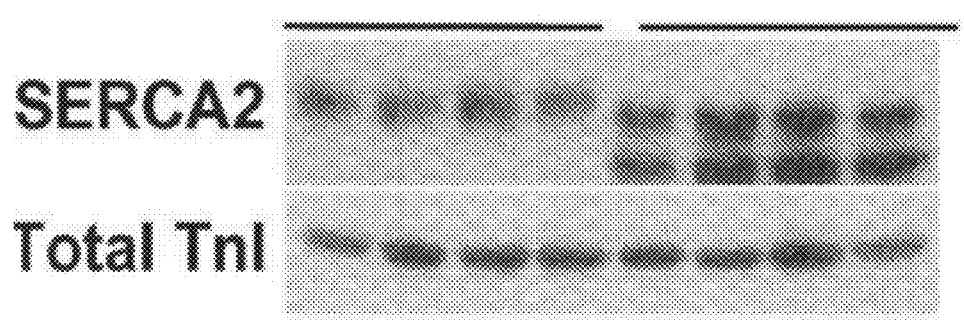
Figure 16A:
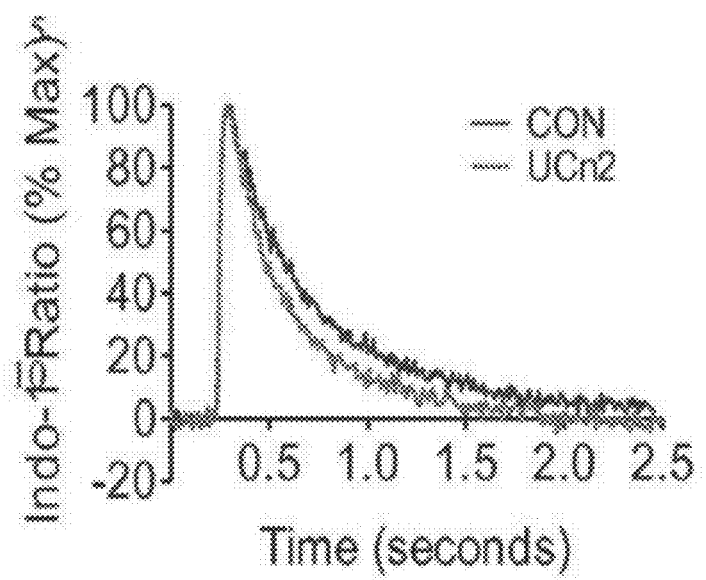
FIG. 16A-B shows data of $Ca^{2+}$ transients following UCn2 gene transfer.
Figure 16B:
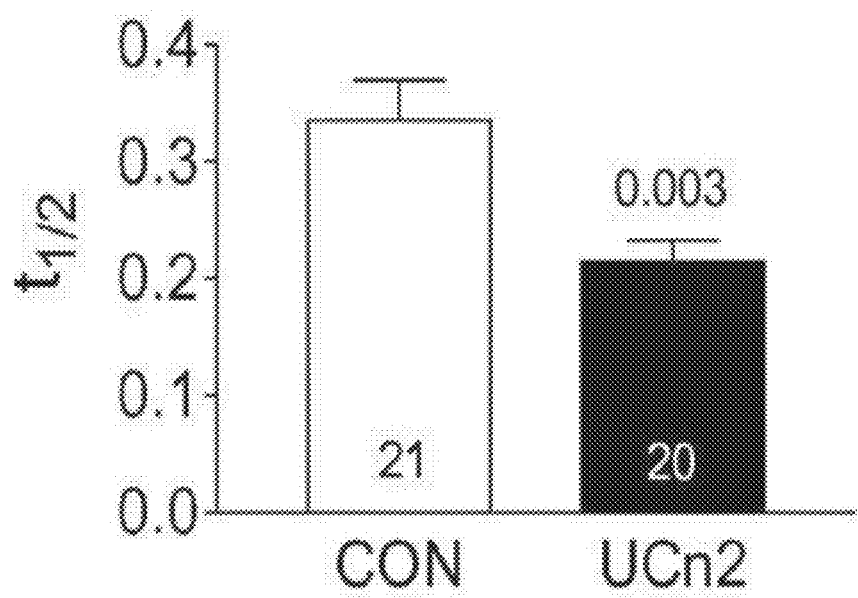

FIG. 15 illustrates data (FIG. 15A, by graph, FIG. 15B, by immunoblot) where normal mice received IV delivery of AAV8.CBA.UCn2 ($5 \times 10^{11}$ gc) or saline (CON); and four weeks later, LV samples from the UCn2 gene transfer group showed a 2-fold increase in SERCA2a protein expression. Immunoblotting signal was normalized to TnI content. Numbers in bars denote group size. These changes in SERCA2a expression would be anticipated to promote $Ca^{2+}$ availability at the myofilament, and thereby increase LV systolic and diastolic function. UCn2 Gene Transfer & $Ca^{2+}$ Transients. Cardiac myocytes (CM) were isolated from mice 4 w after AAV8.CBA.UCn2 ($5 \times 10^{11}$ gc, IV). Mice that had received IV saline were used as controls. During the measurement, cardiac myocytes from UCn2 mice were incubated with 24 nM UCn2 peptide to mimic serum UCn2 levels in vivo. Cardiac myocytes from mice receiving UCn2 gene transfer showed altered $Ca^{2+}$ transients with reduced t1/2, as illustrated in FIG. 16: $Ca^{2+}$ transients following UCn2 gene transfer: FIG. 16A graphically illustrates that UCn2 gene transfer increased the rate of $Ca^{2+}$ decline; FIG. 16B graphically illustrates that time-to-$Ca^{2+}$ transient decay was shortened in cardiac myocytes from mice that had received UCN2 gene transfer 4 w prior. Experiments were repeated three times. Bars denote mean+SE; numbers in bars denote number of cardiac myocytes; numbers above bars indicate p value.

Figure 17A:
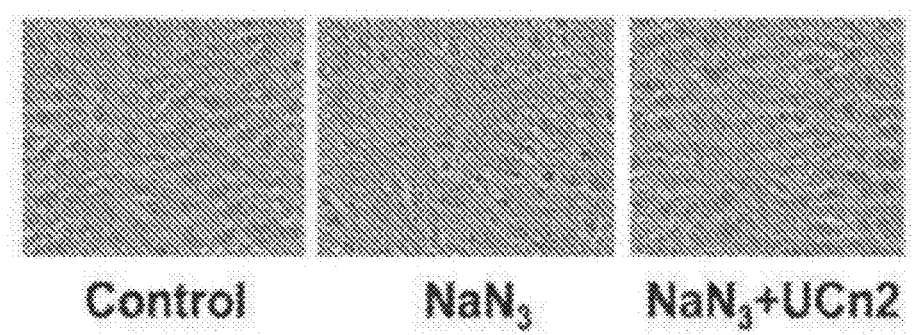
FIG. 17A-B show data that UCn2 protects cultured neonatal rat cardiac myocytes from hypoxic injury.
Figure 17B:
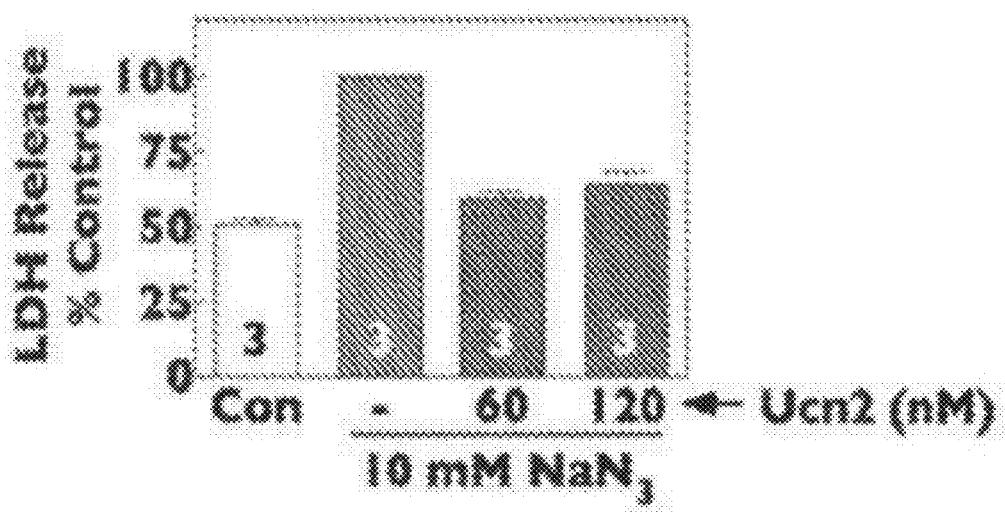

UCn2 is Cardioprotective. To test UCn2's effects on hypoxic injury, we treated cultured neonatal rat cardiac myocytes with sodium azide ($NaN_3$), which irreversibly binds the heme cofactor in cytochrome oxidase and inhibits mitochondrial respiration, mimicking hypoxia-induced cytotoxicity. UCn2 treatment protected cardiac myocytes from injury as reflected morphologically and by reduced LDH release, as illustrated in FIG. 17. UCn2 also protects isolated cardiac myocytes from hypoxia-reoxygenation injury ($p<0.001$; data not shown). FIG. 17 shows data that UCn2 protects cultured neonatal rat cardiac myocytes from hypoxic injury: FIG. 17A illustrates that UCn2 (60 nM) preserves morphological normality 24 hr after $NaN_3$ (10 mM) treatment; FIG. 17B graphically illustrates that UCn2 reduced LDH release after $NaN_3$ treatment ($p<0.001$).

Figure 18A:
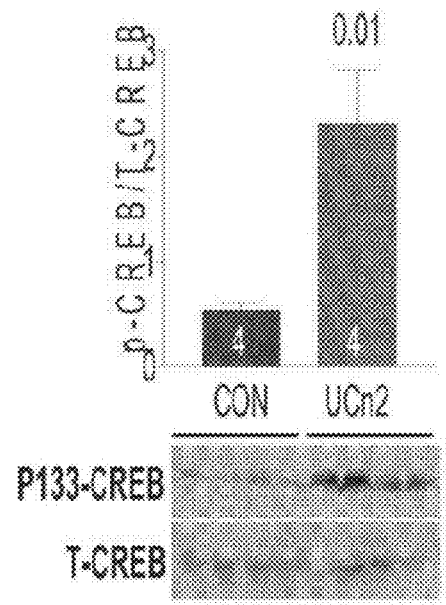
FIG. 18A-B graphically illustrates that phosphorylation of both CREB (FIG. 18A) and β-catenin (FIG. 18B) was detected in LV samples 4 w after IV delivery of the exemplary UCn2.CBA.UCn2 construct of the invention, as described in Example 3, below.
Figure 18B:
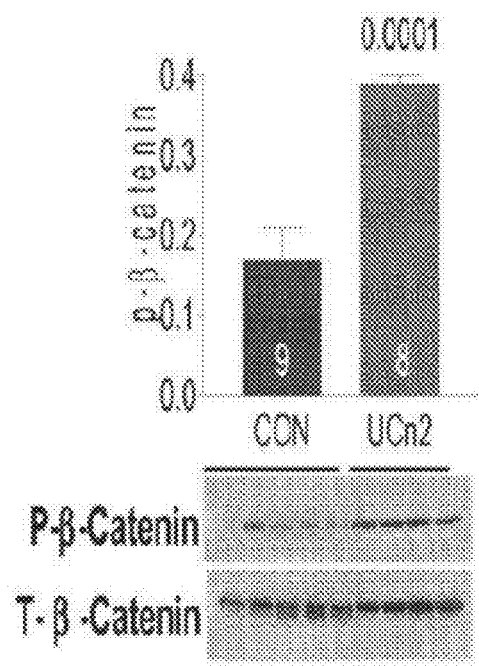

Effects on CREB and β-Catenin. LV samples were obtained from mice 4 w after AAV8.CBA.UCn2 ($5 \times 10^{11}$ gc, IV). Mice that had received IV saline were used as controls. LV samples from mice that had received UCn2 gene transfer showed increased phosphorylation of CREB (a 3-fold increase, $p<0.01$, FIG. 18A). CREB is a transcriptional factor that enables CRE-mediated gene expression in the heart. In addition, UCn2 gene transfer was associated with a 2-fold increase in LV β-catenin phosphorylation ($p<0.0001$, FIG. 18B). Increased β-catenin phosphorylation reduces β-catenin accumulation in the intercalated disks of cardiac myocytes and thereby reduces cardiac stiffness and diastolic dysfunction. This may contribute to our observation that UCn2 gene transfer increases LV relaxation in normal and failing hearts. FIG. 18 graphically illustrates that phosphorylation of both CREB (FIG. 18A) and β-catenin (FIG. 18B) was detected in LV samples 4 w after IV delivery of UCn2.CBA.UCn2. Control mice received IV saline.

Figure 19A:
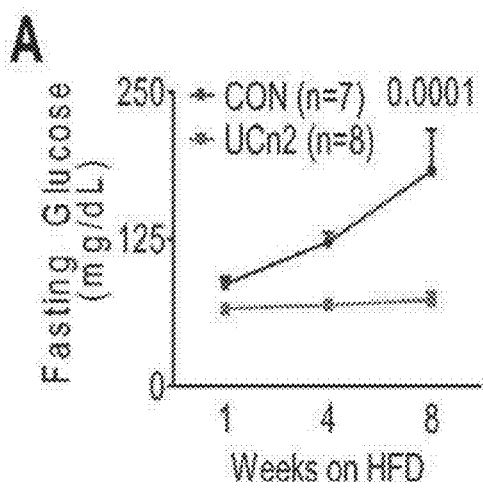
FIG. 19A-B illustrate data showing UCn2 affects glucose regulation: Mice received IV delivery of the exemplary AAV8.CBA.UCn2.
Figure 19B:
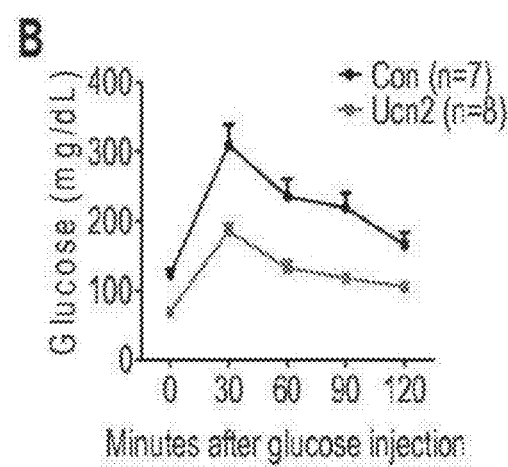
Figure 20A:
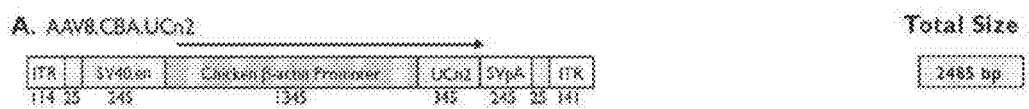
FIG. 20A-F illustrate exemplary constructs of the invention, as described in Example 3, below.
Figure 20B:
Figure 20C:
Figure 20D:
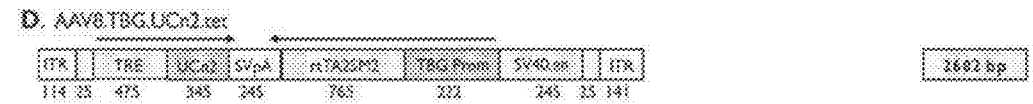
Figure 20E:
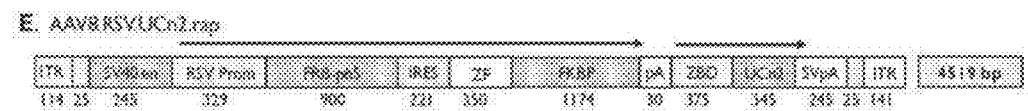
Figure 20F:
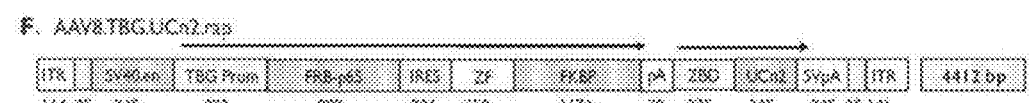

Non-Cardiac Effects of UCn2 Gene Transfer. IV delivery of AAV8.CBA.UCn2 ($5 \times 10^{11}$ gc) has a favorable effect on glucose metabolism—an anti-diabetic effect. For example, mice that received UCn2 gene transfer are resistant to hyperglycemia induced by high fat diet (HFD), a model of Type 2 diabetes used in preclinical studies (FIG. 19A). Reduced glucose levels are due to increased glucose utilization as seen in glucose tolerance testing of HFD-fed mice (FIG. 19B). FIG. 19 illustrates data showing UCn2 affects glucose regulation. Mice received IV delivery of AAV8.CBA.UCn2 ($5 \times 10^{11}$ gc, n=8) or saline (n=8), & standard chow for 3 w. A small reduction in fasting blood glucose was seen in the UCn2 group. Mice then received a high fat diet (HFD) for 8 w. Hyperglycemia was seen in Controls, as expected, but UCn2 mice maintained normal blood glucose levels. FIG. 19B. Mice received IV delivery of AAV8.CBA.UCn2 ($5 \times 10^{11}$ gc, n=8) or saline (n=8) & HFD for 2 months & glucose tolerance tests conducted. Fasted mice received glucose (2 mg/g body weight, IP) and glucose levels measured. Results indicate that UCn2 gene transfer promotes glucose utilization and protects against diet-induced hyperglycemia.

FIG. 20 illustrates exemplary constructs of the invention: Abbreviations: ITR, inverted terminal repeat; TRE, tetracycline response element; SVpA, polyA from SV40 viral genome (bidirectional); rtTA2SM2, reverse tetracycline controlled transactivator; SV40en, simian virus 40 enhancer; TBG Prom, thyroid hormone-binding globulin promoter; RSV Prom, Rous sarcoma virus promoter; FRB-p6, part of FRAP, a rapamycin interacting protein, combined with a subunit of transcription factor NF-κB (p65); IRE, internal transcription reentry site; ZF, zinc finger HD1 DNA binding domain; FKBP, FK506 binding protein; pA, minimal polyadenylation segment; ZBD, zinc finger HD DNA binding domain (8 copies).

Example 4

Akita Mouse Model of Type 1 Diabetes Mellitus Responsive to Urocortin 2 Gene Transfer The Akita Mouse is accepted in the art as a Model for Type 1 Diabetes Mellitus. The mouse is characterized by:
 Spontaneous mutation in Ins2 gene, leading to single amino acid substitution in insulin molecule—a monogenic model of Type 1 Diabetes Mellitus
 Alters insulin folding, which leads to beta-cell toxicity and depletion
 Heterozygotes viable and fertile; homozygotes rarely live 12 weeks Autosomal dominant (easy to breed); male>female phenotype By 4 weeks old: hyperglycemia, polydipsia, polyuria Plasma insulin levels 10-15% of normal mean life span 305 days (normal 690 days); 80% mortality at 1 year Used to evaluate nephropathy, neuropathy, retinopathy The rationale for the experiments, to determine whether urocortin-2 (UCn2) gene transfer would be effective in an insulin deficient (rather than a purely insulin resistant state), was based on data indicating that the mechanism by which UCn2 gene transfer is effective in promoting glucose disposal in insulin resistant states does not affect the usual signaling elements involved in insulin resistance. Instead, it appeared that UCn2 was operating independently of insulin-signaling and promoting glucose disposal via previously undescribed mechanisms. Since Type 1 DM is not generally associated with striking abnormalities in insulin resistance, testing whether UCn2 gene transfer was effective in the Akita mouse would provide supportive data that UCn2's mechanism of action involves an independent pathway for glucose disposal. In addition, such a discovery would have significant impact clinically, potentially providing a new therapeutic approach to patients with Type 1 diabetes.

Figure 21:
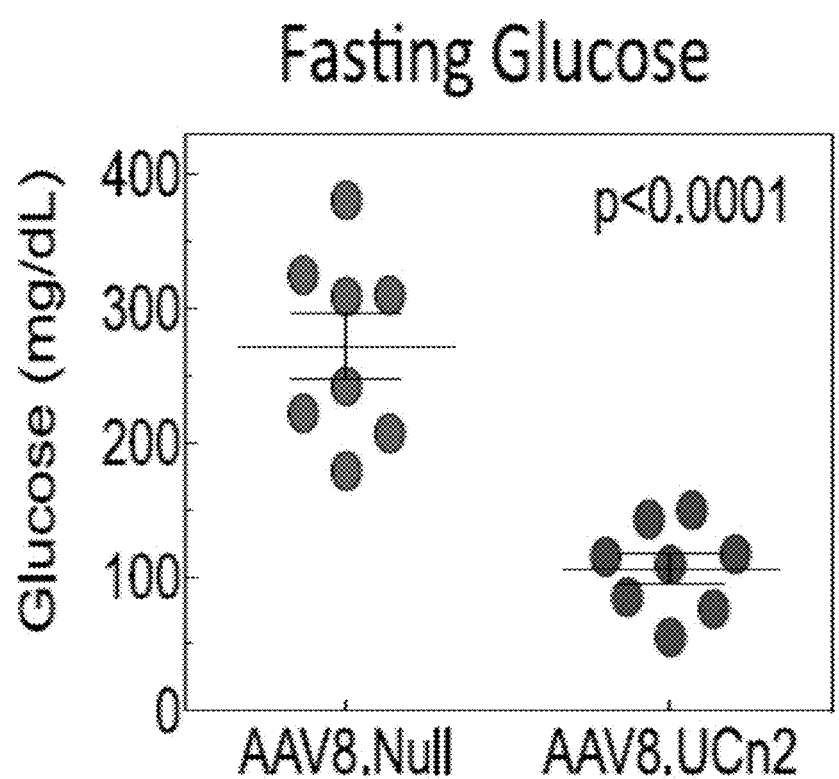
FIG. 21 shows reduced fasting glucose (p<0.0001) in mice that received AAV8.UCn2.
Figure 22:
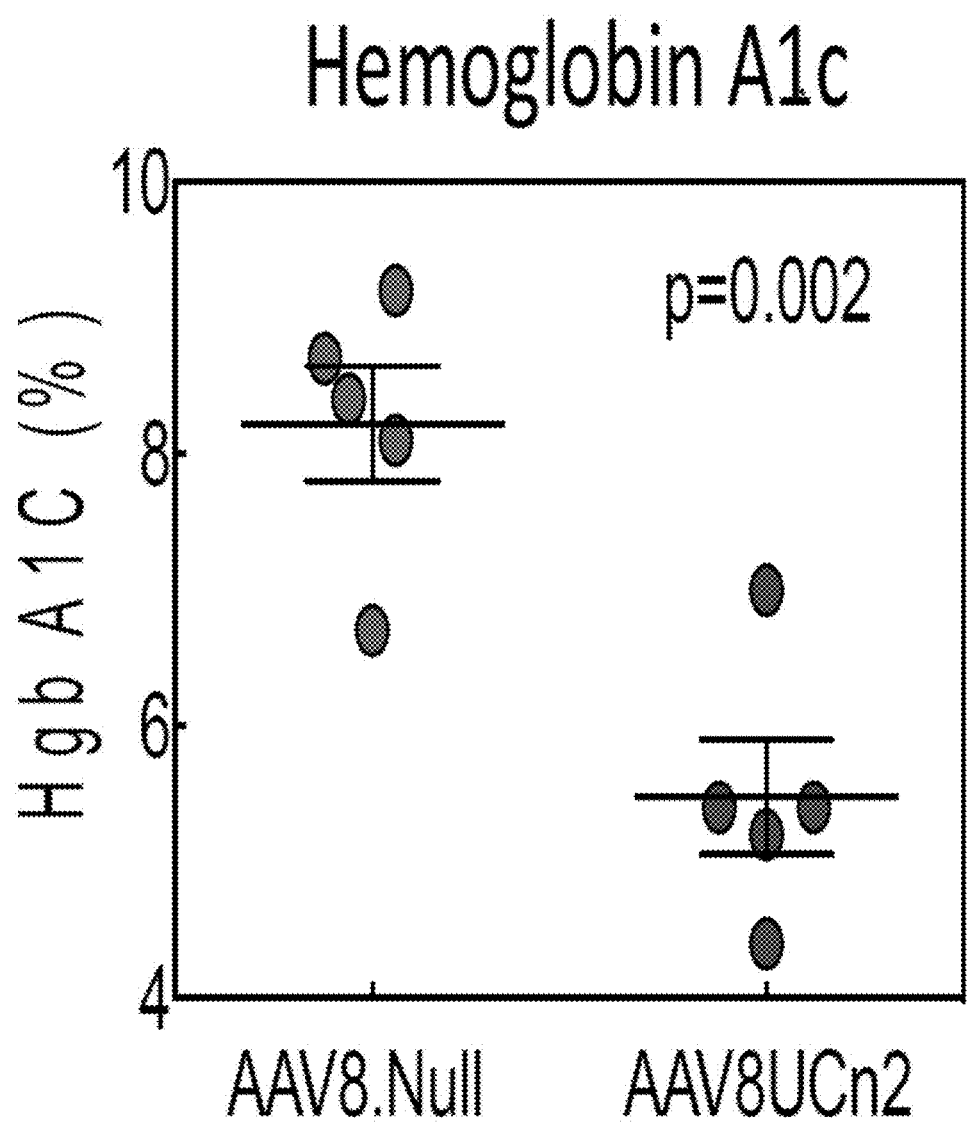
FIG. 22 shows hemoglobin A1C (p=0.002) in mice that received AAV8.UCn2.

Fasting Glucose and Hemoglobin A1c:

Sixteen (16) 3-month old male Akita mice (19 grams body weight) received intravenous (IV) delivery of adeno-associated virus type 8 (AAV8, $2 \times 10^{13}$ genome copies/kg. Eight received AAV8.Null (control) and 8 received AAV8 encoding murine UCn2, both with CBA promoters. Data were collected 8-10 weeks after vector delivery. The results (FIG. 21) show reduced fasting glucose (p<0.0001) in mice that received AAV8.UCn2. Mean fasting glucose was 270 mg/dL in AAV8.Null mice, but was reduced to 108 mg/dL in mice that received AAV8.UCn2. Sustained improvement in glucose control was indicated by significant reductions in hemoglobin A1c (p=0.002) (FIG. 22).

Figure 23:
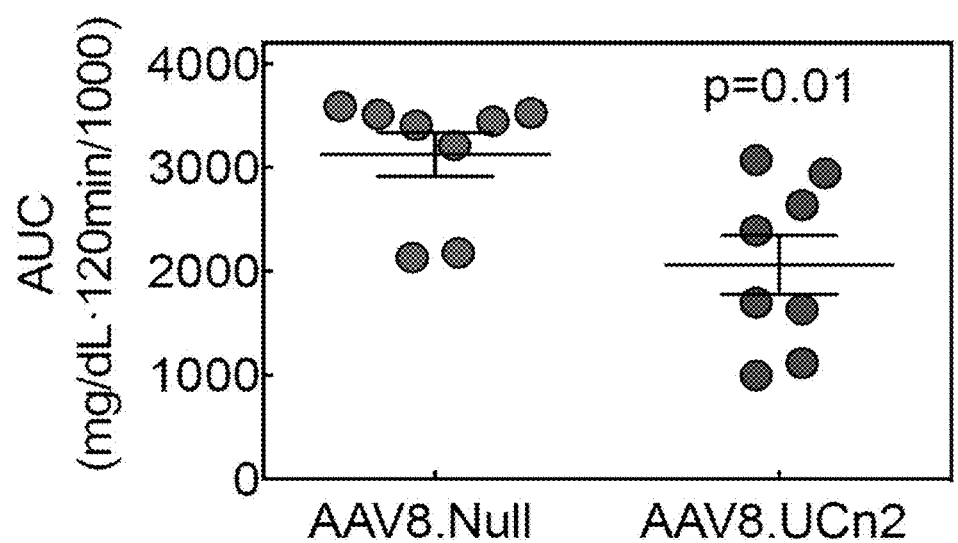
FIG. 23 shows a glucose tolerance test (p=0.01) in mice that received AAV8.UCn2.

Glucose Tolerance Test: The same 16 mice described above underwent glucose tolerance testing to quantify glucose disposal when challenged with a glucose load after a 12-hr fast (2.5 g/kg). These data (FIG. 23) indicate a more rapid glucose disposal rate (p=0.01), as indicated by reduced area under the glucose concentration-time curve. These data, which show some overlap between the two groups, must be confirmed by measuring insulin sensitively using hyperinsulinemic euglycemic clamps, studies that are underway.

Figure 24:
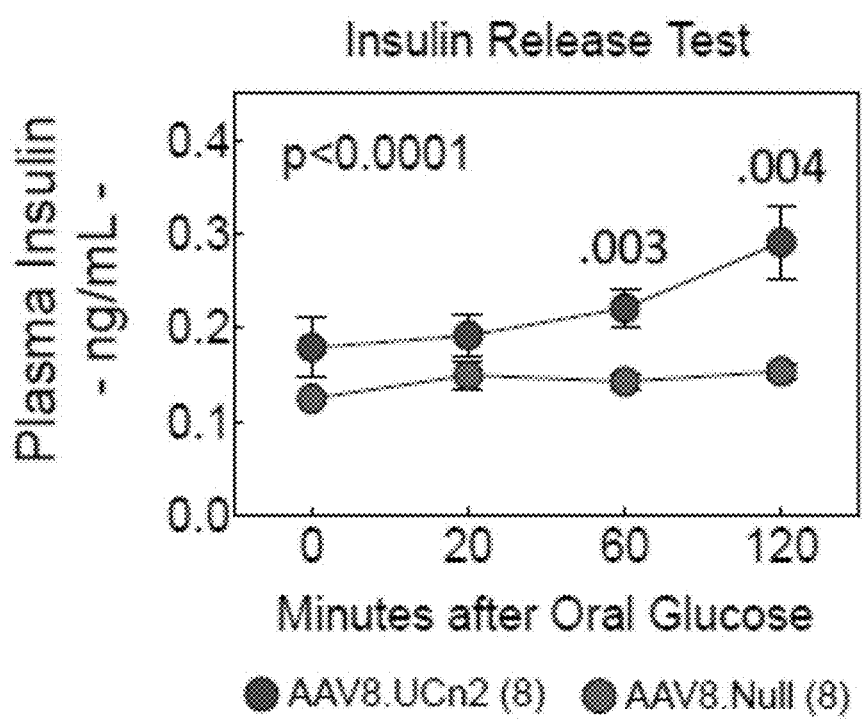
FIG. 24 shows Insulin Release in mice that received AAV8.UCn2 (p=0.003 at 60 min and p=0.004 at 120 min).
Figure 25:
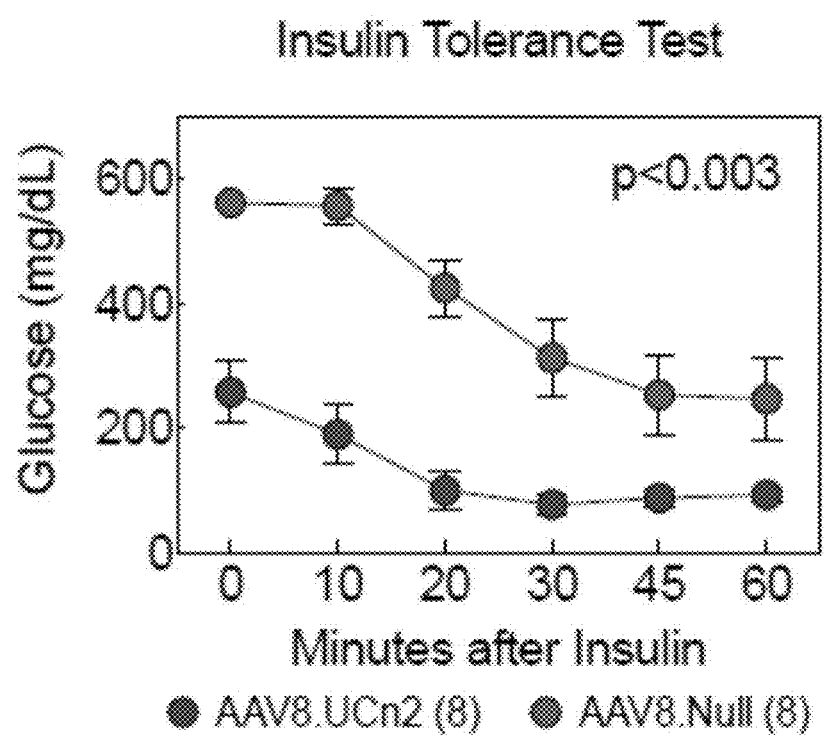
FIG. 25 shows Insulin Tolerance in mice that received AAV8.UCn2 (p<0.003).

Insulin Release and Insulin Tolerance Testing. Because it is plausible that UCn2 may influence insulin release or insulin sensitivity, we tested insulin release (FIG. 24) and insulin tolerance (FIG. 25). Insulin release was assessed after a 12 hr fast followed by an oral glucose load (2.5 g/kg). Insulin tolerance was tested after a 4 hr fast and an insulin challenge (0.75 U/kg, IV). An unexpected finding was that mice that had received UCn2 gene transfer 10 weeks prior, showed superior insulin release both 60 min (p=0.003) and 120 min (p=0.004) after glucose challenge (FIG. 24). Insulin tolerance testing indicated a reduced EC50 for glucose disposal in mice that had received UCn2 gene transfer (FIG. 25; p<0.003).

In summary, the data show that UCn2 gene transfer increases glucose disposal independently of insulin. UCn2 gene transfer increases insulin sensitivity and UCn2 gene transfer may increase glucose-induced insulin release. Thus, these data support the use of UCn2 gene transfer for the treatment of insulin deficient states, such as encountered in clinical Type 1 DM.

REFERENCES

1 Roger V L, Go A S, Lloyd-Jones D M, Benjamin E J, Berry J D, Borden W B et al. Heart disease and stroke statistics—2012 update: a report from the American Heart Association. *Circulation* 2012; 125: e2-e220. PMID: 22179539

2 Nathwani A C, Tuddenham E G, Rangarajan S, Rosales C, McIntosh J, Linch D C et al. Adenovirus-associated virus vector-mediated gene transfer in hemophilia B. *N Engl J Med* 2011; 365: 2357-2365. PMCID: PMC3265081

3 Buchlis G, Podsakoff G M, Radu A, Hawk S M, Flake A W, Mingozzi F et al. Factor IX expression in skeletal muscle of a severe hemophilia B patient 10 years after AAV-mediated gene transfer. *Blood* 2012; in press. PMID: 22271447

4 Flotte T R, Trapnell B C, Humphries M, Carey B, Calcedo R, Rouhani F et al. Phase 2 clinical trial of a recombinant adeno-associated viral vector expressing alpha1-antitrypsin: interim results. *Hum Gene Ther* 2011; 22: 1239-1247. PMCID: PMC3205788

5 Brantly M L, Spencer L T, Humphries M, Conlon T J, Spencer C T, Poirier A et al. Phase I trial of intramuscular injection of a recombinant adeno-associated virus serotype 2 alpha1-antitrypsin (AAT) vector in AAT-deficient adults. *Hum Gene Ther* 2006; 17: 1177-1186. PMID: 17115945

6 De B P, Heguy A, Hackett N R, Ferris B, Leopold P L, Lee J et al. High levels of persistent expression of alpha1-antitrypsin mediated by the nonhuman primate serotype rh.10 adeno-associated virus despite preexisting immunity to common human adeno-associated viruses. *Mol Ther* 2006; 13: 67-76. PMID: 16260185

7 Gao G P, Lu Y, Sun X, Johnston J, Calcedo R, Grant R et al. High-level transgene expression in nonhuman primate liver with novel adeno-associated virus serotypes containing self-complementary genomes. *J Virol* 2006; 80: 6192-6194. PMCID: PMC1472562

8 Nathwani A C, Rosales C, McIntosh J, Rastegarlari G, Nathwani D, Raj D et al. Long-term safety and efficacy following systemic administration of a self-complementary AAV vector encoding human FIX pseudotyped with serotype 5 and 8 capsid proteins. *Mol Ther* 2011; 19: 876-885. PMCID: PMC3098629

9 Stieger K, Le Meur G, Lasne F, Weber M, Deschamps J Y, Nivard D et al. Long-term doxycycline-regulated transgene expression in the retina of nonhuman primates following subretinal injection of recombinant AAV vectors. *Mol Ther* 2006; 13: 967-975. PMID: 16442848

10 Rivera V M, Gao G P, Grant R L, Schnell M A, Zoltick P W, Rozamus L W et al. Long-term pharmacologically regulated expression of erythropoietin in primates following AAV-mediated gene transfer. *Blood* 2005; 105: 1424-1430. PMID: 15507527

11 Lai N C, Tang T, Gao M H, Saito M, Miyanohara A, Hammond H K. Improved function of the failing rat heart by regulated expression of insulin-like growth factor I via intramuscular gene transfer. *Hum Gene Ther* 2012; 23: 255-261. PMID: 22017392

12 Mingozzi F, Meulenberg J J, Hui D J, Basner-Tschakarjan E, Hasbrouck N C, Edmonson S A et al. AAV-1-mediated gene transfer to skeletal muscle in humans results in dose-dependent activation of capsid-specific T cells. *Blood* 2009; 114: 2077-2086. PMCID: PMC2744569

13 Manno C S, Pierce G F, Arruda V R, Glader B, Ragni M, Rasko J J et al. Successful transduction of liver in hemophilia by AAV-Factor IX and limitations imposed by the host immune response. *Nat Med* 2006; 12: 342-347. PMID: 16474400

14 Hildinger M, Auricchio A, Gao G, Wang L, Chirmule N, Wilson J M. Hybrid vectors based on adeno-associated virus serotypes 2 and 5 for muscle-directed gene transfer. *J Virol* 2001; 75: 6199-6203. PMCID: PMC114336

15. Fang H, Lai N C, Gao M H, Miyanohara A, Roth D M, Tang T, Hammond H K. Comparison of adeno-associated virus serotypes and delivery methods for cardiac gene transfer. *Hum Gene Ther Methods* 2012; October 17 [Epub ahead of print] PMID: 23075106

16. Boutin S, Monteilhet V, Veron P, Leborgne C, Benveniste O, Montus M F, Masurier C. Prevalence of serum IgG and neutralizing factors against adeno-associated virus (AAV) types 1, 2, 5, 6, 8, and 9 in the healthy population: implications for gene therapy using AAV vectors. *Hum Gene Ther* 21:704-712, 2010

17. Everett R S, Evans H K, Hodges B L, Ding E Y, Serra D M, Amalfitano A. Strain-specific rate of shutdown of CMV enhancer activity in murine liver confirmed by use of persistent [E1(–), E2b(–)] adenoviral vectors. *Virology* 2004; 325: 96-105. PMID: 15231389

18. Hoppe U C, Marban E, Johns D C. Adenovirus-mediated inducible gene expression in vivo by a hybrid ecdysone receptor. *Mol Ther* 2000; 1: 159-164. PMID: 10933926

19. Sipo I, Wang X, Hurtado Pico A, Suckau L, Weger S, Poller W et al. Tamoxifen-regulated adenoviral E1A chimeras for the control of tumor selective oncolytic adenovirus replication in vitro and in vivo. *Gene Ther* 2006; 13: 173-186. PMID: 16136163

20. Goverdhana S, Puntel M, Xiong W, Zirger J M, Barcia C, Curtin J F et al. Regulatable gene expression systems for gene therapy applications: progress and future challenges. *Mol Ther* 2005; 12: 189-211. PMCID: PMC2676204

21. Rivera V M, Clackson T, Natesan S, Pollock R, Amara J F, Keenan T et al. A humanized system for pharmacologic control of gene expression. *Nat Med* 1996; 2: 1028-1032. PMID: 8782462

22. Stieger K, Belbellaa B, Le Guiner C, Moullier P, Rolling F. In vivo gene regulation using tetracycline-regulatable systems. *Adv Drug Deliv Rev* 2009; 61: 527-541. PMID: 19394373

23. Harrison D E, Strong R, Sharp Z D, Nelson J F, Astle C M, Flurkey K et al. Rapamycin fed late in life extends lifespan in genetically heterogeneous mice. *Nature* 2009; 460: 392-395. PMCID: PMC2786175

24. Villarreal F J, Griffin M, Omens J, Dillmann W, Nguyen J, Covell J. Early short-term treatment with doxycycline modulates postinfarction left ventricular remodeling. *Circulation* 2003; 108: 1487-1492.

25. Lai N C, Tang T, Gao M H, Saito M, Takahashi T, Roth D M et al. Activation of cardiac adenylyl cyclase expression increases function of the failing ischemic heart in mice. *J Am Coll Cardiol* 2008; 51: 1490-1497. PMID: 18402905

26. Stieger K, Mendes-Madeira A, Meur G L, Weber M, Deschamps J Y, Nivard D et al. Oral administration of doxycycline allows tight control of transgene expression: a key step towards gene therapy of retinal diseases. *Gene Ther* 2007; 14: 1668-1673. PMID: 17914405

27. Goverdhana S, Puntel M, Xiong W, Zirger J M, Barcia C, Curtin J F, Soffer E B, Mondkar S, King G D, Hu J, Sciascia S A, Candolfi M, Greengold D S, Lowenstein P R, Castro M G. Regulatable gene expression systems for gene therapy applications: progress and future challenges. *Mol Ther* 12: 189-211, 2005

28. Gao M H, Bayat H, Roth D M, Yao Zhou J, Drumm J, Burhan J et al. Controlled expression of cardiac-directed adenylylcyclase type VI provides increased contractile function. *Cardiovasc Res* 2002; 56: 197-204. PMID: 12393090

29. Tang T, Hammond H K, Firth A, Yang Y, Gao M H, Yuan J X J, Lai N C. Adenylyl cyclase 6 improves calcium uptake and LV function in aged heart. *J Am Coll Cardiol* 2011; 57: 1846-1855. PMID:21527140

30. Urlinger S, Baron U, Thellmann M, Hasan M T, Bujard H, Hillen W. Exploring the sequence space for tetracycline-dependent transcriptional activators: novel mutations yield expanded range and sensitivity. *Proc Natl Acad Sci USA* 97:7963-7968, 2000

31. Rolain J M, Mallet M N, Raoult D. Correlation between serum doxycycline concentrations and serologic evolution in patients with *Coxiella burnetii* endocarditis. *J Infect Dis* 2003; 188: 1322-1325. PMID: 14593588

32. Berman B, Perez O A, Zell D. Update on rosacea and anti-inflammatory-dose doxycycline. *Drugs Today (Banc)* 2007; 43: 27-34. PMID: 17315050

33. Herzog R W, Hagstrom J N, Kung S H, Tai S J, Wilson J M, Fisher K J et al. Stable gene transfer and expression of human blood coagulation factor IX after intramuscular injection of recombinant adeno-associated virus. *Proc Natl Acad Sci USA* 1997; 94: 5804-5809. PMCID: PMC20861

34. Minniti G, Muni R, Lanzetta G, Marchetti P, Enrici R M. Chemotherapy for glioblastoma: current treatment and future perspectives for cytotoxic and targeted agents. *Anticancer Res* 2009; 29: 5171-5184. PMID: 20044633

35. Zoncu R, Efeyan A, Sabatini D M. mTOR: from growth signal integration to cancer, diabetes and ageing. *Nat Rev Mol Cell Biol* 2011; 12: 21-35. PMID: 21157483

36. Yang W, Digits C A, Hatada M, Narula S, Rozamus L W, Huestis C M et al. Selective epimerization of rapamycin via a retroaldol/aldol mechanism mediated by titanium tetraisopropoxide. *Org Lett* 1999; 1: 2033-2035. PMID: 10905864

37. Abraham R T, Wiederrecht G J. Immunopharmacology of rapamycin. *Annu Rev Immunol* 1996; 14: 483-510. PMID: 8717522

38. Davidson S M, Rybka A E, Townsend P A. The powerful cardioprotective effects of urocortin and the corticotropin releasing hormone (CRH) family. *Biochem Pharmacol.* 2009; 77:141-150. PMID: 18817752

39. Perrin M H, Vale W W. Corticotropin releasing factor receptors and their ligand family. *Ann N Y Acad Sci.* 1999; 885:312-328. PMID: 10816663

40. Eckart K, Radulovic J, Radulovic M, Jahn O, Blank T, Stiedl O, Spiess J. Actions of CRF and its analogs. *Curr Med Chem.* 1999; 6:1035-1053. PMID: 10519912

41. Wiley K E, Davenport A P. CRF2 receptors are highly expressed in the human cardiovascular system and their cognate ligands urocortins 2 and 3 are potent vasodilators. *Br J Pharmacol* 2004; 143:508-514. PMCID: PMC1575420

42. Imperatore A, Florio P, Tones P B, Torricelli M, Galleri L, Toti P, Occhini R, Picciolini E, Vale W, Petraglia F. Urocortin 2 and urocortin 3 are expressed by the human placenta, deciduas, and fetal membranes. *Am J Obstet Gynecol.* 2006; 195:288-295. PMID: 16626608

43. Boorse G C, Denver R J. Widespread tissue distribution and diverse functions of corticotropin-releasing factor and related peptides. *Gen Comp Endocrinol.* 2006; 146:9-18. PMID: 16413023

44. Wiley K E, Davenport A P. CRF2 receptors are highly expressed in the human cardiovascular system and their cognate ligands urocortins 2 and 3 are potent vasodilators. Br J Pharmacol 143:508-514,2004

45. Singh L K, Boucher W, Pang X, Letourneau R, Seretakis D, Green M, Theoharides T C. Potent mast cell degranulation and vascular permeability triggered by urocortin through activation of corticotropin-releasing hormone receptors. *J Pharmacol Exp Ther.* 1999; 288:1349-1356. PMID: 10027877

46 Emeto T I, Moxon J V, Rush C, Woodward L, Golledge J. Relevance of urocortins to cardiovascular disease. *J Mol Cell Cardiol.* 2011; 51:299-307. PMID: 21689660

47 Hauger R L, Grigoriadis D E, Dallman M F, Plotsky P M, Vale W W, Dautzenberg F M., International Union of Pharmacology. XXXVI. Current status of the nomenclature for receptors for corticotropin-releasing factor and their ligands. *Pharmacol. Rev.* 2003; 55:21-26. PMID: 12615952

48 Perrin M H, Donaldson C J, Chen R, Lewis K A, Vale W W. Cloning and functional expression of a rat brain corticotropin releasing factor (CRF) receptor. *Endocrinology.* 1993; 133:3058-3061. PMID: 8243338

49 Hinkle R T, Donnelly E, Cody D B, Bauer M B, Isfort R J. Urocortin II treatment reduces skeletal muscle mass and function loss during atrophy and increases nonatrophying skeletal muscle mass and function. Endocrinology 144: 4939-4946, 2003

50 Davis M E, Pemberton C J, Yandle T G, Fisher S F, Lainchbury J G, Frampton C M, Rademaker M T, Richards A M. Urocortin 2 infusion in healthy humans: hemodynamic, neurohormonal, and renal responses. J Am Coll Cardiol. 30:461-741, 2007

51 Davis M E, Pemberton C J, Yandle T G, Fisher S F, Lainchbury J G, Frampton C M, Rademaker M T, Richards M. Urocortin 2 infusion in human heart failure. Eur Heart J 28: 2589-2597, 2007

52 Bale T L, Hoshijima M, Gu Y, Dalton N, Anderson K R, Lee K F, Rivier J, Chien K R, Vale W W, Peterson K L. The cardiovascular physiologic actions of urocortin II: acute effects in murine heart failure. Proc Natl Acad Sci USA 101:3697-3702, 2004

53 Yang L Z, Kockskämper J, Khan S, Suarez J, Walther S, Doleschal B, Unterer G, Khafaga M, Machler H, Heinzel F R, Dillmann W H, Pieske B, Spiess J. cAMP- and $Ca^{2+}$/calmodulin-dependent protein kinases mediate inotropic, lusitropic and arrhythmogenic effects of urocortin 2 in mouse ventricular myocytes. Br J Pharmacol 162:544-56, 2011

54 Meili-Butz S, Bühler K, John D, Buser P, Vale W W, Peterson K L, Brink M, Dieterle T. Acute effects of urocortin 2 on cardiac function and propensity for arrhythmias in an animal model of hypertension-induced left ventricular hypertrophy and heart failure. Eur J Heart Fail. 12:797-804, 2010

55 Brar B K, Jonassen A K, Stephanou A, Santilli G, Railson J, Knight R A, Yellon D M, Latchman D S. Urocortin protects against ischemic and reperfusion injury via a MAPK-dependent pathway. J Biol Chem 275:8508-8514, 2000

56 Brar B K, Jonassen A K, Egorina E M, Chen A, Negro A, Perrin M H, Mjos O D, Latchman D S, Lee K F, Vale W. Urocortin-II and urocortin-III are cardioprotective against ischemia reperfusion injury: an essential endogenous cardioprotective role for corticotropin releasing factor receptor type 2 in the murine heart. Endocrinology 145:24-35, 2004

57 Barry S P, Lawrence K M, McCormick J, Soond S M, Hubank M, Eaton S, Sivarajah A, Scarabelli T M, Knight R A, Thiemermann C, Latchman D S, Townsend P A, Stephanou A. New targets of urocortin-mediated cardioprotection. J Mol Endocrinol 45: 69-85, 2010

58 Rademaker M T, Charles C J, Espiner E A, Fisher S, Frampton C M, Kirkpatrick C M, Lainchbury J G, Nicholls M G, Richards A M, Vale W W. Beneficial hemodynamic, endocrine, and renal effects of urocortin in experimental heart failure: comparison with normal sheep. J Am Coll Cardiol 40:1495-1505, 2002

59 Miriam T, Rademaker M T, Charles C J, Nicholls M G, Richards A M. Urocortin 2 inhibits furosemide-induced activation of renin and enhances renal function and diuretic responsiveness in experimental heart failure. Circ Heart Fail 2: 532-540, 2009

60 Tang W H W, Francis G S. Exploring new drugs for heart failure: the case of urocortin. Eur Heart J 28: 2561-2562, 2007

61 Haurigot V, Mingozzi F, Buchlis G, Hui D J, Chen Y, Basner-Tschakarjan E, Arruda V R, Radu A, Franck H G, Wright J F, Zhou S, Stedman H H, Bellinger D A, Nichols T C, High K A. Safety of AAV factor IX peripheral transvenular gene delivery to muscle in hemophilia B dogs. Mol Ther 18:1318-1329, 2010

62 Roth D A, McKirnan M D, Canestrelli I, Gao M H, Dalton N, Lai N C, Roth D M, Hammond H K. Intracoronary delivery of an adenovirus encoding fibroblast growth factor-4 in myocardial ischemia: effect of serum antibodies and previous exposure to adenovirus. Human Gene Ther 17:230-238, 2006

63 Kaspar B K, Roth D M, Lai N C, Drumm J D, Erickson D A, McKirnan M D, Hammond H K. Myocardial gene transfer and long-term expression following intracoronary delivery of AAV. J Gene Med 7: 316-324, 2005.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating type I diabetes in a mammal, the method comprising: injecting an adeno-associated viral (AAV) vector comprising a nucleic acid sequence encoding Uracortin 2 (UCN2) operably linked to a promoter to a mammal with type I diabetes intravenously such that increased insulin release and decreased hyperglycemia in the mammal occurs.

2. The method of claim 1, wherein the AAV vector is selected from AAV8 or AAV9.

3. The method of claim 1, wherein the promoter is selected from a chicken beta-actin (CBA), thyroid hormone-binding globulin (TBG), or Rous Sarcoma Virus (RSV).

4. The method of claim 1, wherein the subject is a human.

5. The method of claim 1, wherein the subject is a canine, non-human primate or feline subject.

6. The method of claim 1, wherein the mammal exhibits increased glucose control.

7. The method of claim 1, wherein the injecting occurs 1-5 times.

8. The method of claim 1, wherein the AAV vector is an AAV-DJ or AAVrh10 vector.

* * * * *

UNITED STATES PATENT AND TRADEMARK OFFICE
CERTIFICATE OF CORRECTION

PATENT NO. : 10,202,618 B2  
APPLICATION NO. : 15/625719  
DATED : February 12, 2019  
INVENTOR(S) : H. Kirk Hammond and Mei Hua Gao It is certified that error appears in the above-identified patent and that said Letters Patent is hereby corrected as shown below:

On the Title Page  
Under (54) title, please delete "Uracortin" and replace with --Urocortin--

In the Specification  
In Column 1, Line 3, please delete "Uracortin" and replace with --Urocortin--

In the Claims  
In Column 46, Line 43, please delete "Uracortin" and replace with --Urocortin--

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*